(12) United States Patent
Tatsuta et al.

(10) Patent No.: US 11,419,694 B2
(45) Date of Patent: *Aug. 23, 2022

(54) ENDOSCOPE SYSTEM MEASURING SIZE OF SUBJECT USING MEASUREMENT AUXILIARY LIGHT

(71) Applicant: FUJIFILM Corporation, Tokyo (JP)

(72) Inventors: Takeichi Tatsuta, Kanagawa (JP); Shinichiro Sonoda, Kanagawa (JP); Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 487 days.

This patent is subject to a terminal disclaimer.

(21) Appl. No.: 16/543,619

(22) Filed: Aug. 19, 2019

(65) Prior Publication Data

US 2019/0388175 A1 Dec. 26, 2019

Related U.S. Application Data

(63) Continuation of application No. PCT/JP2018/008355, filed on Mar. 5, 2018.

(30) Foreign Application Priority Data

Mar. 28, 2017 (JP) .............................. JP2017-063543

(51) Int. Cl.
*A61B 90/00* (2016.01)
*A61B 1/00* (2006.01)

(52) U.S. Cl.
CPC ............ *A61B 90/06* (2016.02); *A61B 1/0005* (2013.01); *A61B 1/00006* (2013.01);
(Continued)

(58) Field of Classification Search
USPC ....................................................... 600/108
See application file for complete search history.

(56) References Cited

U.S. PATENT DOCUMENTS

| 3,595,220 A | 7/1971 | Kawahara |
| 3,817,635 A | 6/1974 | Kawahara |

(Continued)

FOREIGN PATENT DOCUMENTS

| AT | 502919 | 6/2007 |
| AU | 2002322410 | 2/2008 |

(Continued)

OTHER PUBLICATIONS

"International Search Report (Form PCT/ISA/210) of PCT/JP2018/008355", dated May 22, 2018, with English translation thereof, pp. 1-5.

(Continued)

*Primary Examiner* — John P Leubecker
(74) *Attorney, Agent, or Firm* — JCIPRNET

(57) ABSTRACT

An endoscope system includes a measurement support device and an endoscope. The measurement support device includes a head emitting measurement auxiliary light, an imaging unit capturing an image of a subject on which a spot is formed by the measurement auxiliary light via an imaging optical system, and a processor measuring a position of the spot and displaying an indicator figure. The endoscope includes a memory, an insertion part and an operating part. In a case where the measurement auxiliary light is projected on a plane including an optical axis of the imaging optical system, the measurement auxiliary light has an inclination angle and crosses an angle of view of the imaging optical system. In a case where the indicator figure is displayed in a vicinity of the measured position, the indicator figure is displayed in different aspects according to measurement of the specific region is effective or not.

10 Claims, 23 Drawing Sheets

(52) U.S. Cl.
CPC .... *A61B 1/00009* (2013.01); *A61B 2090/061* (2016.02); *A61B 2090/067* (2016.02)

(56) References Cited

U.S. PATENT DOCUMENTS

| | | | |
|---|---|---|---|
| 4,841,363 A * | 6/1989 | Ams | A61B 1/042 |
| | | | 348/522 |
| 4,935,810 A | 6/1990 | Nonami et al. | |
| 5,090,400 A | 2/1992 | Saito | |
| 5,669,871 A * | 9/1997 | Sakiyama | G01B 11/25 |
| | | | 348/136 |
| 5,693,003 A | 12/1997 | Wolfelschneider et al. | |
| 7,794,388 B2 | 9/2010 | Draxinger et al. | |
| 8,038,602 B2 | 10/2011 | Gill et al. | |
| 8,663,092 B2 * | 3/2014 | Pascal | A61B 1/041 |
| | | | 600/117 |
| 8,724,015 B2 | 5/2014 | Yoshino | |
| 8,858,429 B2 | 10/2014 | Mizuyoshi et al. | |
| 9,215,366 B2 | 12/2015 | Morita | |
| 9,254,075 B2 | 2/2016 | Wolf | |
| 9,691,162 B2 | 6/2017 | Christiansen | |
| 9,739,594 B2 | 8/2017 | Koerner et al. | |
| 9,750,393 B2 | 9/2017 | Wolf | |
| 9,892,512 B2 | 2/2018 | Kuramoto | |
| 10,186,033 B2 | 1/2019 | Kuramoto | |
| 10,317,197 B2 | 6/2019 | Ramachandran et al. | |
| 10,441,150 B2 | 10/2019 | Kuramoto | |
| 2002/0169361 A1 * | 11/2002 | Taniguchi | A61B 1/0005 |
| | | | 600/117 |
| 2005/0240077 A1 * | 10/2005 | Rovegno | G02B 23/2423 |
| | | | 600/117 |
| 2007/0081168 A1 | 4/2007 | Johnston | |
| 2007/0197874 A1 | 8/2007 | Ishihara | |
| 2010/0272318 A1 | 10/2010 | Cabiri et al. | |
| 2011/0074950 A1 | 3/2011 | Oka et al. | |
| 2013/0027548 A1 * | 1/2013 | Gere | G01S 17/08 |
| | | | 348/140 |
| 2013/0110005 A1 | 5/2013 | Sharonov | |
| 2014/0036050 A1 | 2/2014 | Yoshino | |
| 2014/0357986 A1 | 12/2014 | Baldwin | |
| 2015/0222801 A1 * | 8/2015 | Kresser | G03B 17/54 |
| | | | 348/362 |
| 2015/0320296 A1 | 11/2015 | Morita | |
| 2015/0374218 A1 | 12/2015 | Nishio et al. | |
| 2016/0217591 A1 | 7/2016 | Krupnik | |
| 2016/0338590 A1 | 11/2016 | Sagalovich et al. | |
| 2017/0105613 A1 | 4/2017 | Tsuruta et al. | |
| 2019/0069766 A1 | 3/2019 | Mizukura et al. | |

FOREIGN PATENT DOCUMENTS

| | | |
|---|---|---|
| CN | 1550039 | 11/2004 |
| CN | 1695546 | 11/2005 |
| CN | 101208037 | 6/2008 |
| CN | 102469931 | 5/2012 |
| CN | 103068300 | 4/2013 |
| CN | 103120584 | 5/2013 |
| CN | 203693533 | 7/2014 |
| CN | 104146711 | 11/2014 |
| CN | 104271040 | 1/2015 |
| CN | 104434000 | 3/2015 |
| CN | 105025774 | 11/2015 |
| CN | 105050473 | 11/2015 |
| CN | 105105852 | 12/2015 |
| CN | 106163367 | 11/2016 |
| CN | 106419821 | 2/2017 |
| CN | 106455941 | 2/2017 |
| DE | 3629435 | 3/1987 |
| EP | 0403399 | 12/1990 |
| EP | 2263520 | 12/2010 |
| EP | 2666430 | 11/2013 |
| EP | 2843360 | 3/2015 |
| GB | 1233604 | 5/1971 |
| JP | S51045911 | 12/1976 |
| JP | S6249208 | 3/1987 |
| JP | S62073223 | 4/1987 |
| JP | H02216404 | 8/1990 |
| JP | H03231622 | 10/1991 |
| JP | H0473763 | 11/1992 |
| JP | H04323505 | 11/1992 |
| JP | H07136101 | 5/1995 |
| JP | 2002336188 | 11/2002 |
| JP | 2008122759 | 5/2008 |
| JP | 2011015721 | 1/2011 |
| JP | 2011069965 | 4/2011 |
| JP | 2012039255 | 2/2012 |
| JP | 2012222658 | 11/2012 |
| JP | 2017038958 | 2/2017 |
| WO | 2005077272 | 8/2005 |
| WO | 2010071683 | 6/2010 |
| WO | 2012107041 | 8/2012 |
| WO | 2016047191 | 3/2016 |

OTHER PUBLICATIONS

"Written Opinion of the International Searching Authority (Form PCT/ISA/237) of PCT/JP2018/008355", dated May 22, 2018, with English translation thereof, pp. 1-7.

"Search Report of Europe Counterpart Application", dated Jan. 3, 2020, p. 1-p. 8.

Office Action of China Counterpart Application, with English translation thereof, dated Apr. 6, 2021, pp. 1-18.

Wende Zhang et al., "Endoscopic Measuring Ruler", Zhongyuan Medical Journal, vol. 2, Dec. 1990, with Partial English translation, pp. 1-2.

Zeping Wang, "High resolution optical Fourier transform Spectrum measurement method research", Thesis of Master Degree, Ocean University of China, May 2015, pp. 1-66.

Yanjun Li, "Novel All-Fiber Endoscopic Optical Coherence Tomography and Study on the Formation Mechanism of Long Period Fiber Gratings", Thesis of Master Degree, Tianjin University, Jan. 2010, pp. 1-128.

"Office Action of Japan Counterpart Application, Application No. 2019-502861", dated Mar. 19, 2020, with English translation thereof, pp. 1-6.

"Search Report of Europe Counterpart Application, Application No. 18761984.6", dated Mar. 9, 2020, p. 1-p. 7.

"International Search Report (Form PCT/ISA/210) of PCT/JP2018/005058," dated Mar. 27, 2018, with English translation thereof, pp. 1-5.

"Written Opinion of the International Searching Authority (Form PCT/ISA/237) of PCT/JP2018/005058," dated Mar. 27, 2018, with English translation thereof, pp. 1-7.

"Office Action of Europe Counterpart Application, Application No. 18776898.1", dated May 12, 2021, p. 1-p. 5.

"Search Report of Europe Counterpart Application, Application No. 18776898.1", dated Jan. 3, 2020, p. 1-p. 6.

"International Search Report (Form PCT/ISA/210) of PCT/JP2018/008356", dated May 22, 2018, with English translation thereof, pp. 1-5.

"Written Opinion of the International Searching Authority (Form PCT/ISA/237) of PCT/JP2018/008356", dated May 22, 2018, with English translation thereof, pp. 1-7.

"Notice of allowance of U.S. Related Application, U.S. Appl. No. 16/445,216", dated Apr. 1, 2020, p. 1-p. 14.

"Office Action of U.S. Related Application, U.S. Appl. No. 16/543,618", dated Feb. 1, 2022, p. 1-p. 23.

* cited by examiner

FIG. 16

| SPOT | COORDINATES OF POINTS INDICATING MARKER | | | | | |
|---|---|---|---|---|---|---|
| | FIRST | SECOND | ... | j-TH | ... | L-TH |
| P1(X1,Y1) | P11(X1+ΔX11,Y1+ΔY11) | P12(X1+ΔX12,Y1+ΔY12) | ... | P1j(X1+ΔX1j,Y1+ΔY1j) | ... | P1L(X1+ΔX1L,Y1+ΔY1L) |
| P2(X2,Y2) | P21(X2+ΔX21,Y2+ΔY21) | P22(X2+ΔX22,Y2+ΔY22) | ... | P2j(X2+ΔX2j,Y2+ΔY2j) | ... | P2L(X2+ΔX2L,Y2+ΔY2L) |
| P3(X3,Y3) | P31(X3+ΔX31,Y3+ΔY31) | P32(X3+ΔX32,Y3+ΔY32) | ... | P3j(X3+ΔX3j,Y3+ΔY3j) | ... | P3L(X3+ΔX3L,Y3+ΔY3L) |
| ⋮ | ⋮ | ⋮ | ⋮ | ⋮ | ⋮ | ⋮ |
| Pi(Xi,Yi) | Pi1(Xi+ΔXi1,Yi+ΔYi1) | Pi2(Xi+ΔXi2,Yi+ΔYi2) | ... | Pij(Xi+ΔXij,Yi+ΔYij) | ... | PiL(Xi+ΔXiL,Yk+ΔYiL) |
| ⋮ | ⋮ | ⋮ | ⋮ | ⋮ | ⋮ | ⋮ |
| PK(XK,YK) | PK1(XK+ΔXK1,YK+ΔYK1) | PK2(XK+ΔXK2,YK+ΔYK2) | ... | PKj(XK+ΔXKj,YK+ΔYKj) | ... | PKL(XK+ΔXKL,YK+ΔYKL) |

FIG. 17

| | C01 | V01 | A01 |
|---|---|---|---|
| | MARKER DISPLAY | ON | ▼ |
| | C02 | V02 | A02 |
| | ACTUAL SIZE OF MARKER | 5mm | ▼ |
| | C03 | V03 | A03 |
| | ASPECT OF MARKER IN MEASUREMENT EFFECTIVE REGION | SOLID CIRCLE | ▼ |
| | C04 | V04 | A04 |
| | COLOR OF MARKER IN MEASUREMENT EFFECTIVE REGION | WHITE | ▼ |
| | C05 | V05 | A05 |
| | ASPECT OF MARKER IN MEASUREMENT NON-EFFECTIVE REGION | DOTTED CIRCLE | ▼ |
| | C06 | V06 | A06 |
| | COLOR OF MARKER IN MEASUREMENT NON-EFFECTIVE REGION | RED | ▼ |
| | C07 | V07 | A07 |
| | TRAJECTORY DISPLAY | ON | ▼ |
| | C08 | V08 | A08 |
| | IDENTIFICATION DISPLAY OF MEASUREMENT EFFECTIVE REGION | ON | ▼ |

B01 OK    B02 CANCEL    B03 CLEAR

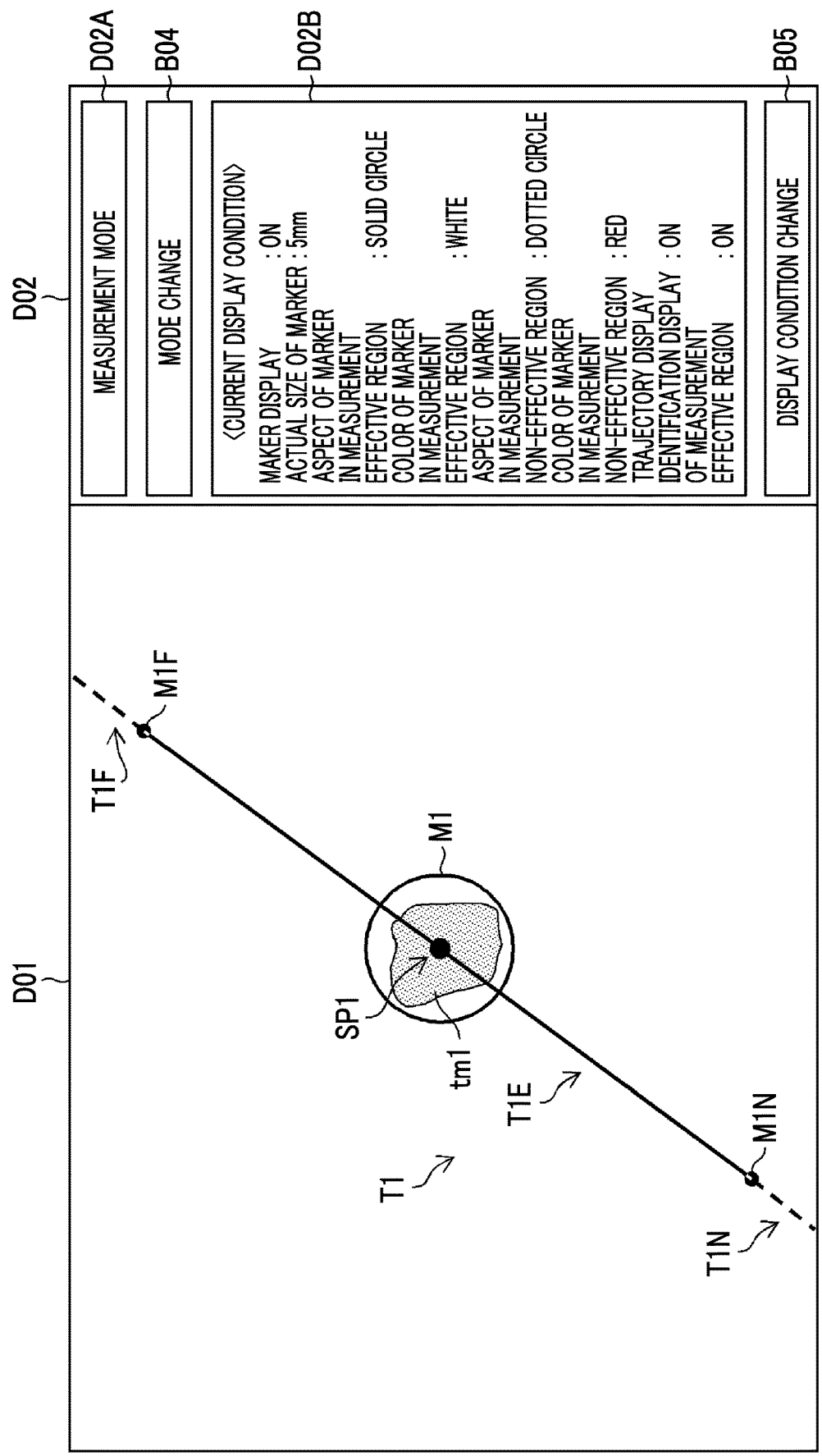

| IMAGE FILE | COORDINATES OF SPOTS |
|---|---|
| IMG001.jpg | P1(X1, Y1) |
| IMG002.jpg | P1(X2, Y2) |
| ... | ... |
| IMGkkk.jpg | PK(XK, YK) |

| IMAGE FILE | COORDINATES OF SPOT | COORDINATES OF POINTS INDICATING MARKER |
|---|---|---|
| IMG001.jpg | P1(X1, Y1) | P11, P12, ⋯, P1j, ⋯, P1L |
| IMG002.jpg | P1(X2, Y2) | P21, P22, ⋯, P2j, ⋯, P2L |
| ⋯ | ⋯ | ⋯ |
| IMGkkk.jpg | Pk(Xk, Yk) | Pk1, Pk2, ⋯, Pkj, ⋯, PkL |

ENDOSCOPE SYSTEM MEASURING SIZE OF SUBJECT USING MEASUREMENT AUXILIARY LIGHT

CROSS-REFERENCE TO RELATED APPLICATIONS

The present application is a Continuation of PCT International Application No. PCT/JP2018/008355 filed on Mar. 5, 2018 claiming priority under 35 U.S.C § 119(a) to Japanese Patent Application No. 2017-063543 filed on Mar. 28, 2017. Each of the above applications is hereby expressly incorporated by reference, in their entirety, into the present application.

BACKGROUND OF THE INVENTION

1. Field of the Invention

The present invention relates to a measurement support device, an endoscope system, and a processor (a processor for an endoscope system), and particularly, to a measurement support device, an endoscope system, and a processor that measure a size of a subject using measurement auxiliary light.

2. Description of the Related Art

In the field of measurement devices such as endoscopes, measuring a distance to a subject or calculating the length and the size of the subject is performed. For example, JP2008-122759A discloses that a subject distance is measured by a stereoscopic camera, the size of a mark serving as a standard of the size of a subject is calculated on the basis of the subject distance and the angle of view of an endoscope, and the mark is displayed together with an image of the subject, and thus the size of the subject can be known from this mark.

Additionally, JP1995-136101A (JP-H07-136101A) discloses a technique of obtaining a distance to an observed part (observation target) and the size of the observed part, using measurement light. In JP1995-136101A (JP-H07-136101A), resolving power in the distance from a distal end of an endoscope insertion part to the observed part and the position of the observed part is improved by radiating the measurement light obliquely with respect to a radiation direction of the illumination light. Additionally, JP1995-136101A (JP-H07-136101A) discloses that a ruler image is displayed to be superimposed on an acquired image and is used for measurement.

SUMMARY OF THE INVENTION

In the above-described JP2008-122759A, two cameras are needed in order to measure the distance with the stereoscopic camera, and a distal end part of the endoscope becomes large. Thus, a burden on the subject becomes high. Moreover, since the distance measurement is performed and the size of the mark is calculated on the basis of the measurement result, the system configuration and processing become complicated.

In the case of endoscopic observation, the subject often has irregularities. In this case, the imaging optical system does not confront the subject. For this reason, a measurement indicator is most likely to be an indicator of a size at a position where a spot of the measurement light hits, and becomes inaccurate as an indicator as the indicator goes away from the position of the spot. Therefore, in a case where the ruler image is moved to any position and rotated by any angle as in JP1995-136101A (JP-H07-136101A), the measurement indicator is likely to be inaccurate as an indicator. In addition, in the endoscope, a wide angle lens is often used, and in this case, distortion is large in the periphery of the image or the like, and thus effective measurement (accurate measurement) is difficult. Further, in a case where the imaging distance is short, an indicator figure (a marker, a ruler figure, and the like) may extend beyond a display range, and in a case where the imaging distance is long, the indicator figure and the measurement target become smaller in the image. In either case, effective measurement is difficult.

In some cases, measurement may not be effective due to the measurement situation as described above, but in the related art, such circumstances are not taken into consideration, and thus it is difficult to perform effective measurement.

The invention has been made in view of such circumstances, and an object thereof is to provide a measurement support device, an endoscope system, and a processor (a processor for an endoscope system) capable of easily performing effective measurement.

In order to achieve the above-described object, a measurement support device related to a first aspect of the invention comprises: a head configured to emit measurement auxiliary light; an imaging unit configured to capture an image of a subject on which a spot is formed by the measurement auxiliary light via an imaging optical system and an imaging element; a measurement unit configured to measure a position of the spot in the image; a display control unit configured to display an indicator figure, which indicates an actual size of a specific region in the subject and has a size set according to the position of the spot in the image, in the vicinity of the position of the spot in the image of the subject, in which, in a case where an optical axis of the measurement auxiliary light is projected on a plane including an optical axis of the imaging optical system, the head emits the measurement auxiliary light that has an inclination angle, which is not 0 degrees with respect to the optical axis of the imaging optical system, and crosses an angle of view of the imaging optical system, and in a case where the indicator figure is displayed in the vicinity of the measured position of the spot, the display control unit displays the indicator figure in different aspects between a case where measurement of the specific region by the displayed indicator figure is effective and a case where measurement of the specific region by the displayed indicator figure is not effective.

According to the aspect, in a case where the indicator figure (marker) is displayed in the vicinity of the spot position, since the indicator figure is displayed in different aspects between a case where measurement of the specific region by the displayed indicator figure is effective and a case where measurement of the specific region by the displayed indicator figure is not effective, it is possible to easily grasp effectiveness of measurement by the display aspect of the indicator figure, and thus effective measurement can be easily performed. In addition, in the first aspect, since the indicator figure (marker) having a size set according to the position of the spot is displayed, distance measurement is not necessary, the configuration is simple, and the processing load is low. Further, since the indicator figure is displayed in the vicinity of the position of the spot (for example, the indicator figure is displayed to be centered on the position of the spot), the difference between the spot position and the marker position is accurate as at least an indicator, and since the indicator figure is not displayed in a wide range, the processing load is low.

In the aspect and each aspect to be described below, an image of a subject and an indicator figure can be displayed on a display device such as various monitors and displays. In addition, in the aspect, since the position of the spot in the image corresponds to the imaging distance, in a case where spot positions are different, display sizes of the marker in the displayed image are different even when the indicator figure has the same actual size.

Further, according to the aspect, the optical axis of the measurement auxiliary light has the inclination angle, which is not 0 degrees with respect to the optical axis of the imaging optical system, and crosses the angle of view of the imaging optical system, in a case where the optical axis of the measurement auxiliary light is projected on the plane including the optical axis of the imaging optical system. Thus, by setting the inclination angle appropriately, the measurement auxiliary light can enter the visual field of the imaging optical system even in a case where the observation distance is short. Moreover, since the optical axis of the measurement auxiliary light has the inclination angle that is not 0 degrees with respect to the optical axis of the imaging optical system in a case where the optical axis of the measurement auxiliary light is projected on the plane including the optical axis of the imaging optical system, the sensitivity of a change in the position of the spot to a change in the observation distance is high, and measurement accuracy is high.

In this manner, with the measurement support device related to the aspect of the invention, effective measurement can be easily performed. In the aspect, the display of the indicator figure may be performed in real time (single time for each frame that a spot image is acquired or for every plural frames), or may be performed offline (in a case where an image on which a spot is formed is acquired, the display of the indicator figure can be performed through post-processing).

In the measurement support device related to a second aspect of the invention, in the first aspect, in a case where the position of the spot is within a measurable region set for the image, the display control unit may determine that measurement of the specific region by the indicator figure is effective. The second aspect indicates an aspect of a determination reference of measurement effectiveness, and the "measurable region" can be set to a part of the movement trajectory of the spot (a central portion of the angle of view or the like), for example.

In the measurement support device related to a third aspect, in the first or second aspect, in a case where an imaging distance of the image calculated on the basis of the position of the spot is within a measurable range, the display control unit may determine that measurement of the specific region by the indicator figure is effective. The third aspect indicates another aspect of a determination reference of measurement effectiveness. For example, a relationship between the imaging distance and the spot position is measured in advance by acquiring an image on which a spot is formed while the imaging distance is changed, and a distance can be calculated by referring to the relationship according to the measured spot position.

In the measurement support device related to a fourth aspect, in any one of the first to third aspects, the display control unit may display the indicator figure by changing at least one of a color or a shape of the indicator figure between a case where measurement of the specific region by the indicator figure is effective and a case where measurement of the specific region by the indicator figure is not effective. Depending on the characteristics of the imaging optical system, for example, distortion may increase at the peripheral part of the angle of view, and accurate measurement may be difficult in such a region. Further, there may be a case where the imaging distance is too short and the indicator figure becomes large and extends beyond the image display range, or a case where the imaging distance is too long, the indicator figure becomes small, and measurement becomes difficult. In view of such circumstances, in the fourth aspect, the indicator figure is displayed by changing at least one of a color or a shape of the indicator figure between a region where measurement of the specific region by the indicator figure is effective and a region where measurement of the specific region by the indicator figure is not effective, and thus the effectiveness of the measurement in the vicinity of the spot position can be easily determined.

The measurement support device related to a fifth aspect, in any one of the first to fourth aspects, may further comprise an image recording unit configured to record the image of the subject on which the spot is formed, in which the display control unit may read the image of the subject recorded in the image recording unit, and display the indicator figure to be superimposed on the read image of the subject. According to the fifth aspect, by recording the image of the subject on which the spot is formed, in the image recording unit, and displaying the indicator figure to be superimposed on the image of the subject read from the image recording unit, post-measurement, that is, the offline measurement can be performed. In this manner, it is possible to shorten a time during which the measurement support device is used for the subject, and to reduce the burden on the subject. In the fifth aspect, by storing the image of the subject and the position of the spot in an association manner, it is possible to display the indicator figure to be superimposed on the image read from the image recording unit. Further, the indicator figure can be displayed by referring to the relationship between the spot position and points constituting the indicator figure.

In the measurement support device related to a sixth aspect, in the fifth aspect, the image recording unit may record the image of the subject and the indicator figure in an association manner, and the display control unit may read the indicator figure and the image of the subject which are recorded in the image recording unit, and display the read indicator figure to be superimposed on the read image of the subject. In the sixth aspect, as "the image of the subject and the indicator figure being in an association manner", for example, the image of the subject and points constituting the indicator figure can be stored in an association manner, and thus the indicator figure can be swiftly and easily displayed.

In the measurement support device related to a seventh aspect, in any one of the first to sixth aspects, the display control unit may display, as the indicator figure, a circle indicating the actual size, which is centered on the spot, to be superimposed on the image. According to the seventh aspect, since the indicator figured is centered on the spot, the indicator figure is accurate as an indicator, and since the circle indicating the actual size is displayed, it is possible to measure an actual size in the entire circumferential direction.

In the measurement support device related to an eighth aspect, in any one of the first to seventh aspects, the display control unit may display information indicating a trajectory along which the spot moves on the image when an imaging distance of the image is changed, to be superimposed on the image. According to the eighth aspect, since the information indicating the movement trajectory of the spot when the imaging distance is changed is displayed, it is easy to move the spot to be in the vicinity of the measurement target (for example, the specific region such as a tumor) by changing the imaging distance, and the measurement can be swiftly and easily performed.

In order to achieve the above-described object, an endoscope system related to a ninth aspect comprises: the measurement support device related to any one of the first to eighth aspects; and an endoscope including an insertion part which is to be inserted into the subject, and has a distal end hard part, a bending part connected to a proximal end side of the distal end hard part, and a flexible part connected to a proximal end side of the bending part, and an operating part connected to a proximal end side of the insertion part, in which the head and an imaging lens that forms an optical image of the spot on the imaging element are provided in the distal end hard part. Since the endoscope system related to the ninth aspect comprises the measurement support device related to any one of the first to eighth aspects, the effective measurement can be easily performed.

In the endoscope system related to a tenth aspect, in the ninth aspect, the endoscope may comprise an information storage unit configured to store information indicating the indicator figure. By the endoscope comprising the information storage unit configured to store the information indicating the indicator figure as in the tenth aspect, it is possible to cope with various types of endoscopes as the whole endoscope system.

The endoscope system related to an eleventh aspect, in the ninth or tenth aspect, may further comprise a display condition setting unit configured to set a display condition of the indicator figure. According to the eleventh aspect, the user can perform measurement with desired display conditions.

In order to achieve the above-described object, a processor related to a twelfth aspect is a processor for the endoscope system related to any one of the ninth to eleventh aspects. The processor comprises the measurement unit and the display control unit. According to the twelfth aspect, as in the first aspect, the effective measurement can be easily performed.

The processor related to a thirteenth aspect, in the twelfth aspect, may further comprise an information acquisition unit configured to acquire information of the endoscope, in which the display control unit may determine whether measurement of the specific region by the displayed indicator figure is effective on the basis of the acquired information. By determining the effectiveness of the measurement on the basis of the information of the endoscope connected to the processor as in the thirteenth aspect, the processor can cope with various endoscopes.

As described above, with the measurement support device, the endoscope system, and the processor (processor for an endoscope system) according to the embodiments of the invention, effective measurement can be easily performed.

BRIEF DESCRIPTION OF THE DRAWINGS

FIG. 16 is a view illustrating a state where a spot position and coordinates of points indicating a circular marker are stored in an association manner.

FIG. 17 is a view illustrating an example of a display condition setting screen.

FIG. 20 is a view illustrating an example of a screen on which a marker and a movement trajectory of a spot are displayed.

DESCRIPTION OF THE PREFERRED EMBODIMENTS

Hereinafter, embodiments of a measurement support device, an endoscope system, and a processor (a processor for an endoscope system) according to the invention will be described in detail, referring to the accompanying drawings.

First Embodiment

Figure 1:
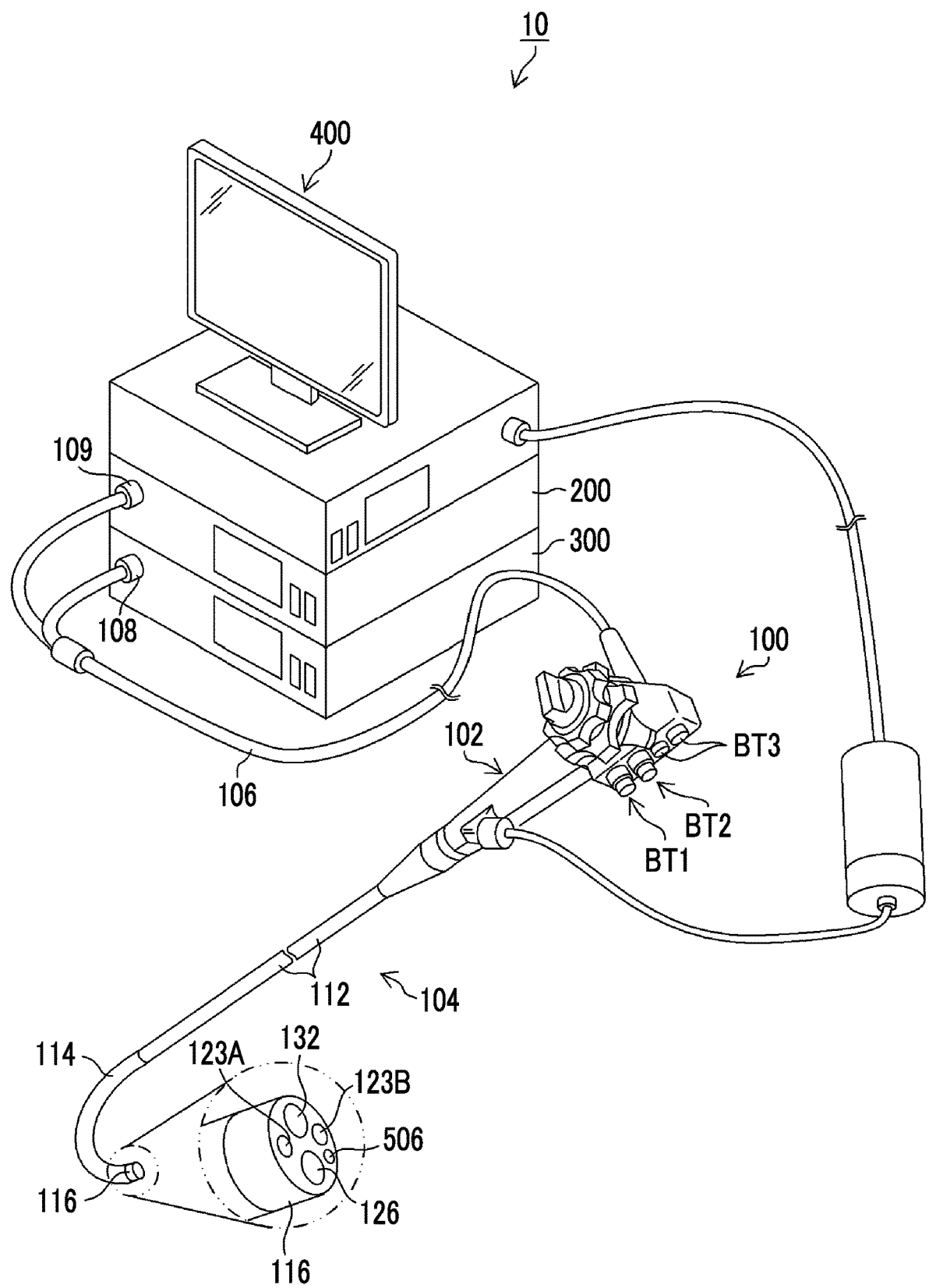
FIG. 1 is a view illustrating an entire configuration of an endoscope system according to a first embodiment of the invention.
Figure 2:
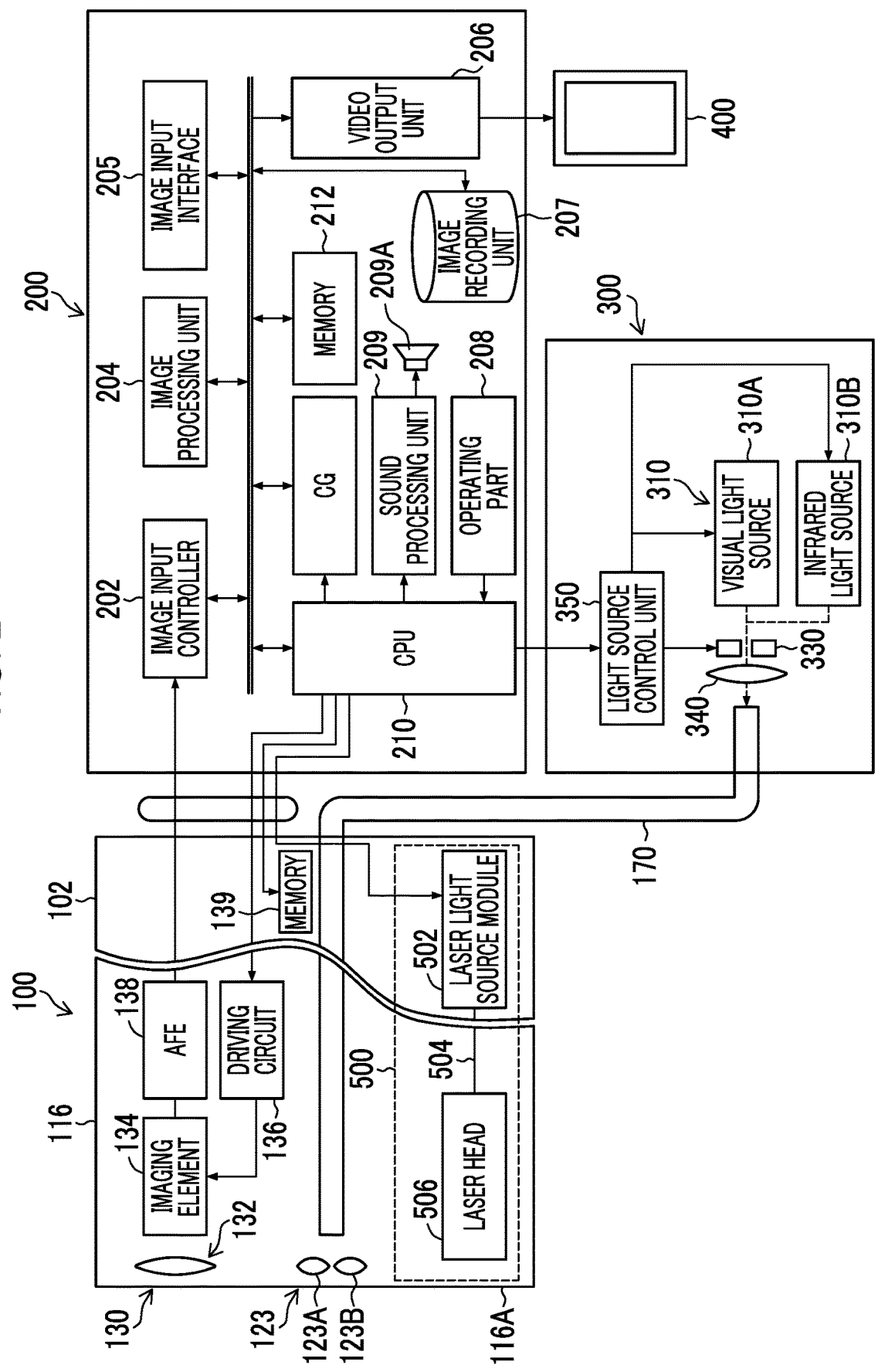
FIG. 2 is a block diagram illustrating the configuration of the endoscope system according to the first embodiment of the invention.

FIG. 1 is an external view illustrating an endoscope system 10 (measurement support device, endoscope system, and processor) according to a first embodiment, and FIG. 2 is a block diagram illustrating the configuration of main parts of the endoscope system 10. As illustrated in FIGS. 1 and 2, the endoscope system 10 includes an endoscope body 100 (endoscope), a processor 200 (processor), a light source device 300, and a monitor 400 (display device).

<Configuration of Endoscope Body>

The endoscope body 100 comprises a proximal operating part 102 (operating part), and an insertion part 104 (insertion part) provided to be connected to the proximal operating part 102. An operator grips the proximal operating part 102, and inserts the insertion part 104 into the body of a subject to observe the body. The proximal operating part 102 is provided with a memory 139 (information storage unit), and information indicating a circular marker (indicator figure) that indicates an actual size of a specific region in the subject and has a size set according to a position of a spot in the image is stored in the memory 139. Information indicating a trajectory along which the spot moves on the image when the imaging distance is changed is also stored in the memory 139, and is displayed in accordance with a display condition setting operation via an operating part 208 or the like. As the memory 139, a non-volatile recording medium (non-temporary recording medium) such as a read only memory (ROM), an electronically erasable and programmable read only memory (EEPROM) can be used. In addition, the proximal operating part 102 is provided with an air-supply and water-supply button BT1, a suction button BT2, and a function button BT3 to which various functions (switching between a normal mode and a measurement mode, and the like) can be assigned. The insertion part 104 is constituted of a flexible part 112 (flexible part), a bending part 114 (bending part), and a distal end hard part 116 (distal end hard part) sequentially from the proximal operating part 102 side. By operating the proximal operating part 102, the bending part 114 can be bent to change the orientation of the distal end hard part 116 vertically and horizontally. The distal end hard part 116 is provided with an imaging optical system 130 (imaging optical system and imaging unit), an illumination unit 123, a forceps port 126, a laser module 500, and the like (refer to FIGS. 1 to 3). A case in which the memory 139 is provided in the proximal operating part 102 is described in FIG. 2, but the memory 139 may be provided in a light guide connector 108 or may be provided in an electrical connector 109 which connects the processor 200 and the endoscope body 100 (refer to FIG. 1).

During observation or treatment, visible light, infrared light, or both can be radiated from illumination lenses 123A and 123B of the illumination unit 123 by the operation of the operating part 208 (refer to FIG. 2). Additionally, washing water is released from a water supply nozzle (not illustrated) by the operation of the air-supply and water-supply button BT1, so that an imaging lens 132 (imaging lens) of the imaging optical system 130 and the illumination lenses 123A and 123B can be washed. A pipe line (not illustrated) communicates with the forceps port 126 that opens at the distal end hard part 116, and a treatment tool (not illustrated) for tumor removal or the like is inserted through the pipe line and is appropriately moved forward and backward so as to perform treatment required for the subject.

Figure 3:
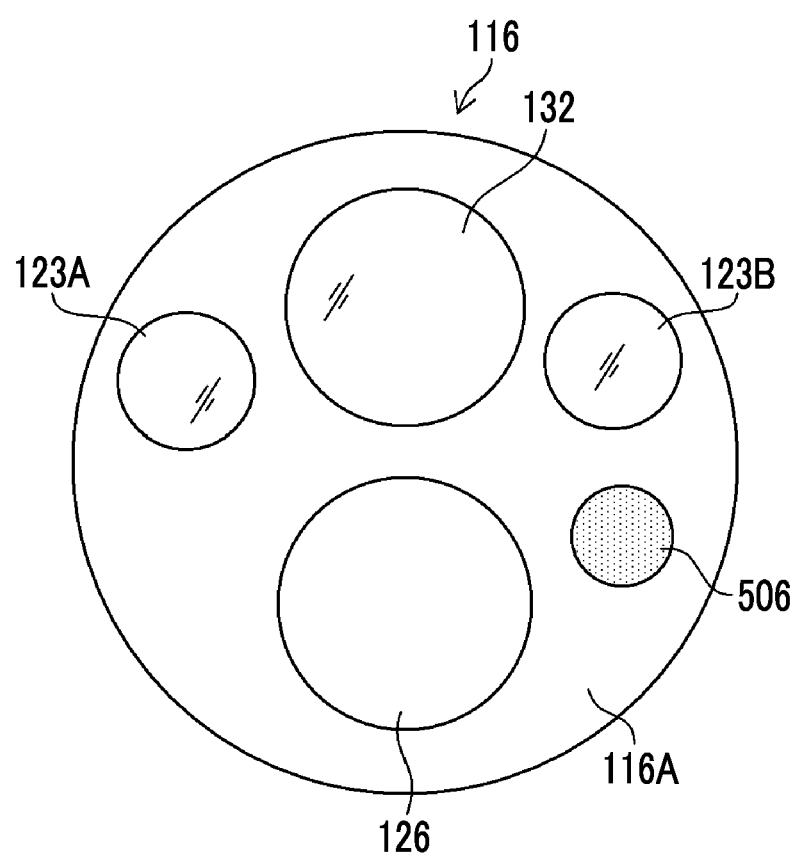
FIG. 3 is a view illustrating a configuration of a distal-end-side end surface of a distal end hard part.

As illustrated in FIGS. 1 to 3, the imaging lens 132 is disposed on a distal-end-side end surface 116A of the distal end hard part 116. A complementary metal-oxide semiconductor (CMOS) type imaging element 134 (imaging element and imaging unit), a driving circuit 136, and an analog front end (AFE) 138 are disposed at the back of the imaging lens 132 so as to output image signals. The imaging element 134 is a color imaging element, and comprises a plurality of pixels constituted of a plurality of light receiving elements arranged in a matrix (two-dimensional array) in a specific pattern arrangement (Bayer arrangement, X-Trans (registered trademark) arrangement, honeycomb arrangement, or the like). Each pixel of the imaging element 134 includes a microlens, a red (R), green (G), or blue (B) color filter, and a photoelectric conversion part (photodiode or the like). The imaging optical system 130 can generate a color image from pixel signals of three colors of red, green, and blue, or can generate an image from pixel signals of any one color or two colors among red, green, and blue. In addition, in the first embodiment, a case where the imaging element 134 is a CMOS type imaging element is described. However, the imaging element 134 may be of charge coupled device (CCD) type.

An image of the subject (a tumor part or a lesion part) or an optical image of a spot (to be described below) is formed on a light-receiving surface (imaging surface) of the imaging element 134 by the imaging lens 132, and is converted into electrical signals, and the electrical signals are output to the processor 200 via a signal cable (not illustrated) and are converted into video signals. Accordingly, an observation image, a circular marker, and the like are displayed on the monitor 400 connected to the processor 200. A touch panel may be provided on the monitor 400 for performing the display condition setting operation (refer to FIGS. 17 to 20) to be described below via a screen.

Additionally, the illumination lens 123A (for visible light) and the illumination lens 123B (for infrared light) of the illumination unit 123 are provided on the distal-end-side end surface 116A of the distal end hard part 116 so as to be adjacent to the imaging lens 132. An exit end of a light guide 170 to be described below is disposed at the back of the illumination lenses 123A and 123B, the light guide 170 is inserted through the insertion part 104, the proximal operating part 102, and a universal cable 106, and an incidence end of the light guide 170 is disposed within the light guide connector 108.

Figure 4:
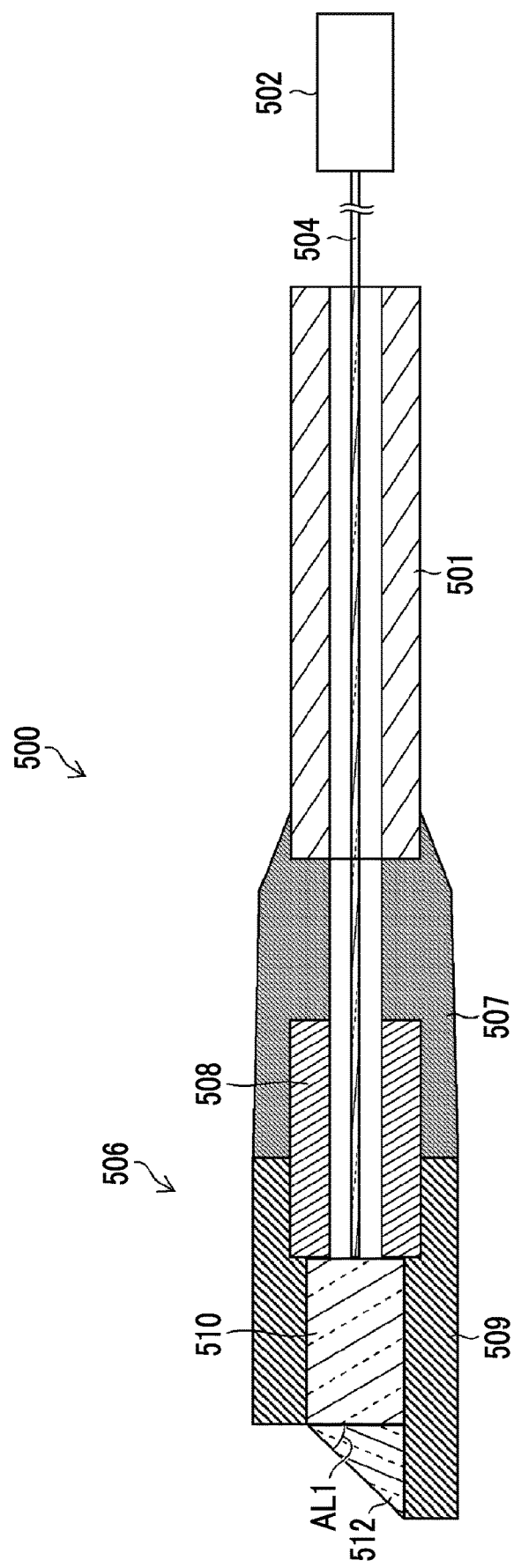
FIG. 4 is a view illustrating a configuration of a laser module.

The distal-end-side end surface 116A is further provided with a laser head 506 (head) of the laser module 500, and the laser head 506 radiates spot light (measurement auxiliary light) via a prism 512 (refer to FIG. 4). The configuration of the laser module 500 will be described later. In addition, in the first embodiment, as illustrated in FIG. 3, the laser head 506 is provided separately from the forceps port 126. However, the laser head 506 may be removably inserted through the pipe line (not illustrated) communicating with the forceps port 126 that opens at the distal end hard part 116. Additionally, the laser head 506 may be provided between the imaging lens 132 and the forceps port 126.

<Configuration of Laser Module>

As illustrated in FIGS. 2 and 4, the laser module 500 comprises a laser light source module 502, an optical fiber 504, and a laser head 506 (head). A proximal end side (laser light source module 502 side) of the optical fiber 504 is covered with a fiber covering 501, a distal end side (a side from which laser light is emitted) thereof is inserted into and is bonded to a ferrule 508 by an adhesive, and an end surface is polished. A graded index (GRIN) lens 510 is mounted on a distal end side of the ferrule 508, and the prism 512 is mounted on a distal end side of the GRIN lens 510 so as to form a joined body. The ferrule 508 is a member for holding and connecting the optical fiber 504, and a hole for allowing the optical fiber 504 to be inserted therethrough is made empty in an axial direction (leftward-rightward direction of FIG. 4) at a central part of the ferrule. A reinforcing member 507 is provided outside the ferrule 508 and the fiber covering 501 to protect the optical fiber 504 or the like. The ferrule 508, the GRIN lens 510, and the prism 512 are housed in a housing 509 and are integrated with the reinforcing member 507 and the fiber covering 501 to constitute the laser head 506.

In the laser head 506, for example, one having a diameter of 0.8 mm to 1.25 mm can be used as the ferrule 508. A fine-diameter ferrule is more preferable for miniaturization. By virtue of the above-described configuration, the total diameter of the laser head 506 can be 1.0 mm to 1.5 mm.

The laser module 500 configured in this way is mounted in the insertion part 104. Specifically, as illustrated in FIG. 2, the laser light source module 502 is provided at the proximal operating part 102, the laser head 506 is provided at the distal end hard part 116, and the optical fiber 504 guides the laser light from the laser light source module 502 to the laser head 506. In addition, the laser light source module 502 may be provided within the light source device 300 so as to guide the laser light to the distal end hard part 116 with the optical fiber 504.

Figure 5:
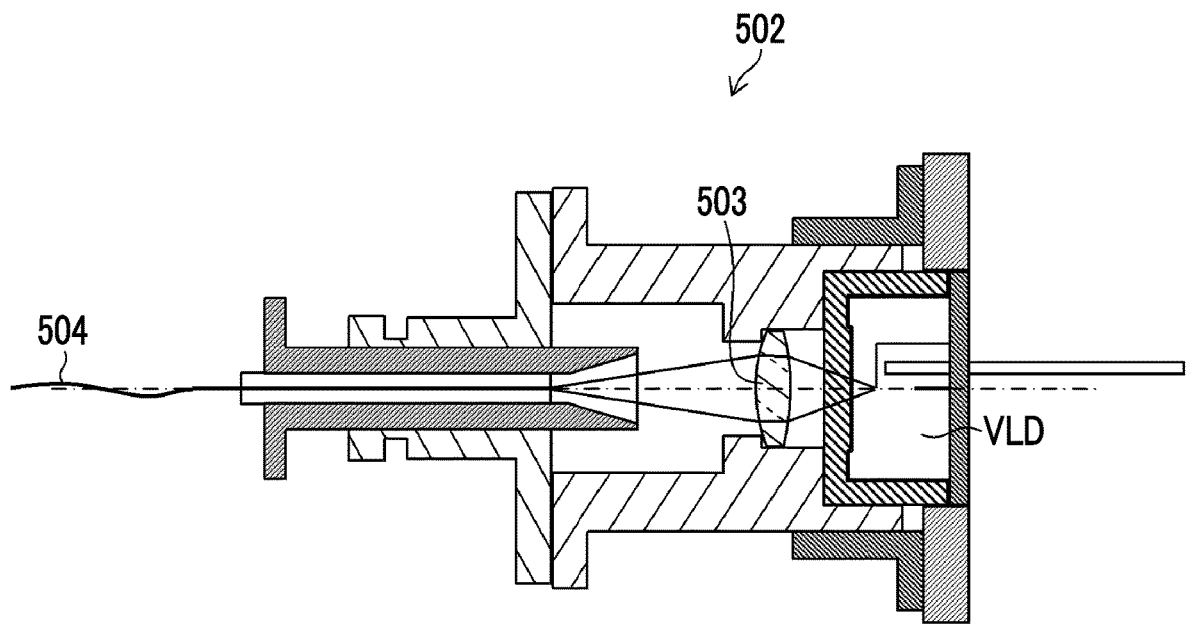
FIG. 5 is a sectional view illustrating a configuration of a laser light source module.

As illustrated in FIG. 5, the laser light source module 502 is a pigtail type module (transmitter optical sub-assembly (TOSA)) comprising a visible laser diode (VLD) that is supplied with electrical power from a power source (not illustrated) and emits laser light, and a condensing lens 503 that condenses the laser light emitted from the VLD. The laser light can be emitted as necessary by the control of the processor 200 (CPU 210). By emitting the laser light only in a case where measurement is performed (measurement mode), the endoscope body can be used similarly to a normal endoscope during non-emission of laser light (normal mode).

In the first embodiment, the laser light emitted by the VLD can be red laser light with a wavelength of 650 nm by a semiconductor laser. However, the wavelength of the laser light in the invention is not limited to this aspect. The laser light condensed by the condensing lens 503 is guided up to the GRIN lens 510 by the optical fiber 504. The optical fiber 504 is an optical fiber that propagates the laser light in a single transverse mode, and can form a clear spot with a small diameter, so that the size of the subject (measurement target) can be accurately measured. A relay connector may be provided in the middle of the optical fiber 504. In addition, in a case where the size of the diameter or clearness of the spot does not pose a measurement problem depending on observation conditions such as the type or size of the subject, an optical fiber that propagates the laser light in a multi-mode may be used as the optical fiber 504. Additionally, as the light source, a light-emitting diode (LED) may be used instead of the semiconductor laser, or the semiconductor laser may be used in an LED light emission state equal to or less than an oscillation threshold value.

The GRIN lens 510 is a cylindrical graded index type lens (radial type) of which the refractive index is highest on the optical axis and decreases radially outward, and functions as a collimator that makes the laser light, which is guided by the optical fiber 504 and enters, into a parallel beam and emits the parallel beam. The spread of the beam emitted from the GRIN lens 510 can be adjusted by adjusting the length of the GRIN lens 510, and about $\lambda/4$ pitch ($\lambda$ is the wavelength of the laser light) or the like may be used to emit the laser light as the parallel beam.

The prism 512 is mounted on a distal end side of the GRIN lens 510. The prism 512 is an optical member for changing the emission direction of the measurement auxiliary light. By changing the emission direction, in a case where the optical axis of the measurement auxiliary light is projected on a plane including the optical axis of the imaging optical system, the optical axis of the measurement auxiliary light has an inclination angle, which is not 0 degrees with respect to the optical axis of the imaging optical system, and the measurement auxiliary light crosses the angle of view of the imaging optical system. The prism 512 is formed to have a size close to the lens diameter of the GRIN lens 510, and a distal end surface thereof is cut obliquely so that the prism 512 has an apex angle AL1 according to the above-described inclination angle. The value of the apex angle AL1 can be set in accordance with the emission direction of the laser light and other conditions.

<Relationship between Optical Axis of Imaging Optical System and Optical Axis of Measurement Auxiliary Light>

Figure 6:
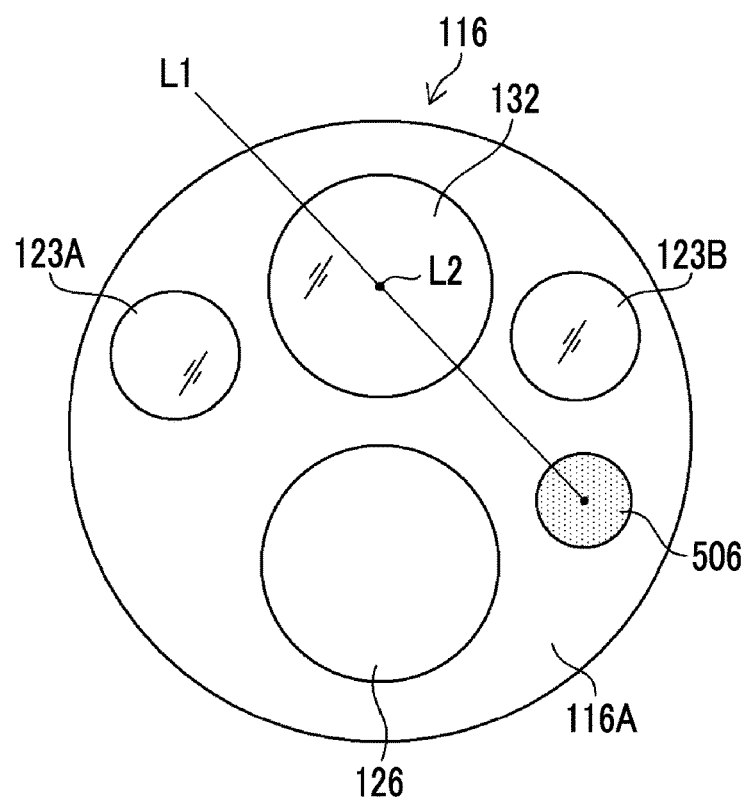
FIG. 6 is a view illustrating a relationship between an optical axis of an imaging optical system, and an optical axis of measurement auxiliary light.

FIG. 6 is a view illustrating a state where the distal end hard part 116 according to the first embodiment is seen from the front (subject side), and is a view corresponding to the configuration of FIG. 3. In the first embodiment, an optical axis L1 of the measurement auxiliary light and an optical axis L2 of the imaging optical system are present on the same plane and intersect each other on the same plane. Hence, in a case where the distal end hard part 116 is seen from the front (subject side), as illustrated in FIG. 6, the optical axis L1 appears to pass on the optical axis L2.

In addition, the relationship between the optical axis L1 of the measurement auxiliary light and the optical axis L2 of the imaging optical system in the invention may not be limited to the above-described aspect in which "the optical axis of the measurement auxiliary light and the optical axis of the imaging optical system are present on the same plane and intersect each other on the same plane", and the optical axis of the measurement auxiliary light may not be present on the same plane as the optical axis of the imaging optical system. However, even in such a case, in a case where the optical axis of the measurement auxiliary light is projected on the plane including the optical axis of the imaging optical system, the optical axis of the measurement auxiliary light has the inclination angle, which is not 0 degrees with respect to the optical axis of the imaging optical system, and crosses the angle of view of the imaging optical system.

In a case where the measurement using the measurement auxiliary light is performed, if the optical axis of the measurement auxiliary light is parallel to the optical axis of the imaging optical system (the inclination angle is 0 degrees), the distance up to a point where the optical axis of the measurement auxiliary light crosses the angle of view of the imaging optical system becomes long depending on the spacing between the optical axes. As a result, a spot cannot be imaged in a closest distance, and the measurement becomes difficult. Additionally, if the optical axis of the measurement auxiliary light is parallel to the optical axis of the imaging optical system, there is a case where the sensitivity of a spot position change with respect to a change in observation distance is low and sufficient measurement accuracy is not obtained. In contrast, as in the first embodiment, a configuration "in a case where the optical axis of the measurement auxiliary light is projected on the plane including the optical axis of the imaging optical system, the optical axis of the measurement auxiliary light has the inclination angle, which is not 0 degrees with respect to the optical axis of the imaging optical system, and crosses the angle of view of the imaging optical system" is adopted. With this configuration, the measurement can be made at an observation distance of a wide range from the closest distance to a long distance. Additionally, since the sensitivity of the spot position change with respect to the distance change is high, the measurement can be made with high accuracy.

<Configuration of Light Source Device>

As illustrated in FIG. 2, the light source device 300 is constituted of a light source 310 for illumination, a stop 330, a condensing lens 340, a light source control unit 350, and the like, and makes illumination light (the visible light or infrared light) incident on the light guide 170. The light source 310 comprises a visible light source 310A and an infrared light source 310B, and is capable of radiating one or both the visible light and the infrared light. The illuminance of the illumination light by the visible light source 310A and the infrared light source 310B is controlled by the light source control unit 350, and the illuminance of the illumination light can be lowered or the illumination can be stopped as necessary in a case where a spot is imaged and measured (in the measurement mode).

By coupling the light guide connector 108 (refer to FIG. 1) to the light source device 300, the illumination light radiated from the light source device 300 is transmitted to the illumination lenses 123A and 123B via the light guide 170 and is radiated to an observation range from the illumination lenses 123A and 123B.

<Configuration of Processor>

Next, the configuration of the processor 200 (a measurement unit, a display control unit, a display condition setting unit, and an information acquisition unit) will be described with reference to FIG. 2. The processor 200 receives the image signals output from the endoscope body 100 via an image input controller 202, and performs required image processing by an image processing unit 204 (the measurement unit, the display control unit, the display condition setting unit, and the information acquisition unit) to output the image signals via a video output unit 206. Accordingly, an observation image is displayed on the monitor 400 (display device). These kinds of processing are performed under the control of a central processing unit (CPU) 210. That is, the CPU 210 has functions as the measurement unit, the display control unit, the display condition setting unit, and the information acquisition unit. In the image processing unit 204, switching and superimposition display of images displayed on the monitor 400, electronic zooming processing, display of images according to operation modes, extraction of a specific component (for example, a brightness signal) from the image signals, and the like are performed in addition to image processing, such as white balance adjustment. Additionally, the image processing unit 204 performs measurement of spot positions on the imaging surface of the imaging element 134, calculation of the size (the number of pixels) of a marker based on the measured positions, and the like (will be described below). An image of the subject on which the spot is formed is recorded in an image recording unit 207. A sound processing unit 209 outputs a warning message (sound) at the time of display condition setting through a speaker 209A under the control of the CPU 210 and the image processing unit 204.

Examples of the specific hardware structure of the image processing unit 204 include processors (electric circuits) such as a central processing unit (CPU), a field programmable gate array (FPGA), and an application specific integrated circuit (ASIC). The image processing unit 204 may be constituted of one processor, or may be constituted of a combination of a plurality of processors. The memory 212 (storage unit) includes a storage element for temporary storage during various processing and a nonvolatile storage element (a non-temporary recording medium), and coordinates of spots, and coordinates of points indicating the circular marker indicating the actual size of the measurement target in the subject are stored in the memory 212 in an association manner (will be described below) under the control of the CPU 210 and/or the image processing unit 204. Additionally, computer-readable codes of the program that makes the CPU 210 and/or the image processing unit 204 execute a measurement support method to be described below are stored in the memory 212.

Additionally, the processor 200 comprises the operating part 208. The operating part 208 comprises an operation mode setting switch (not illustrated) and the like, and can operate radiation of the visible light and/or the infrared light. Additionally, the operating part 208 includes devices such as a keyboard and a mouse, which are not illustrated, and the user can input various processing conditions, display conditions, and the like via these devices. The display condition setting by the operating part 208 will be described below in detail (refer to FIGS. 17 to 20). The setting of the operation mode may be performed by assigning operation mode setting functions (switching between the measurement mode and the normal mode and the like) to the function button BT3 (refer to FIG. 1) of the proximal operating part 102 as described above.

<Observation by Endoscope>

Figure 7:
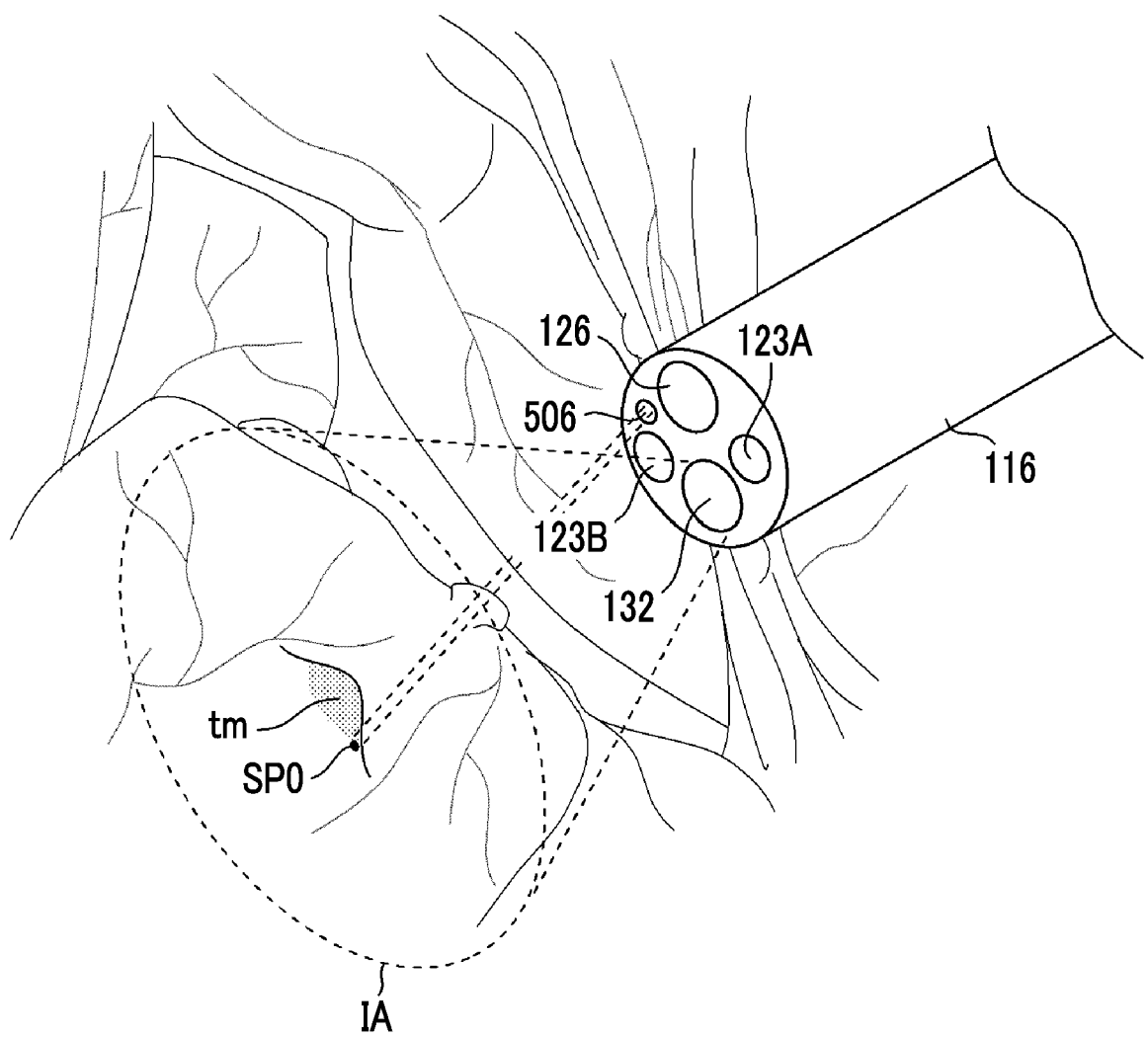
FIG. 7 is a view illustrating a state where an insertion part of the endoscope is inserted into a subject.

FIG. 7 is a view illustrating a state where the insertion part 104 of the endoscope body 100 is inserted into the subject, and illustrates a state where an observation image is acquired for an imaging range IA via the imaging optical system 130. FIG. 7 illustrates a state where a spot SP0 is formed in the vicinity of a tumor tm (a portion that bulges in black).

<Flow of Measurement Processing>

Figure 8:
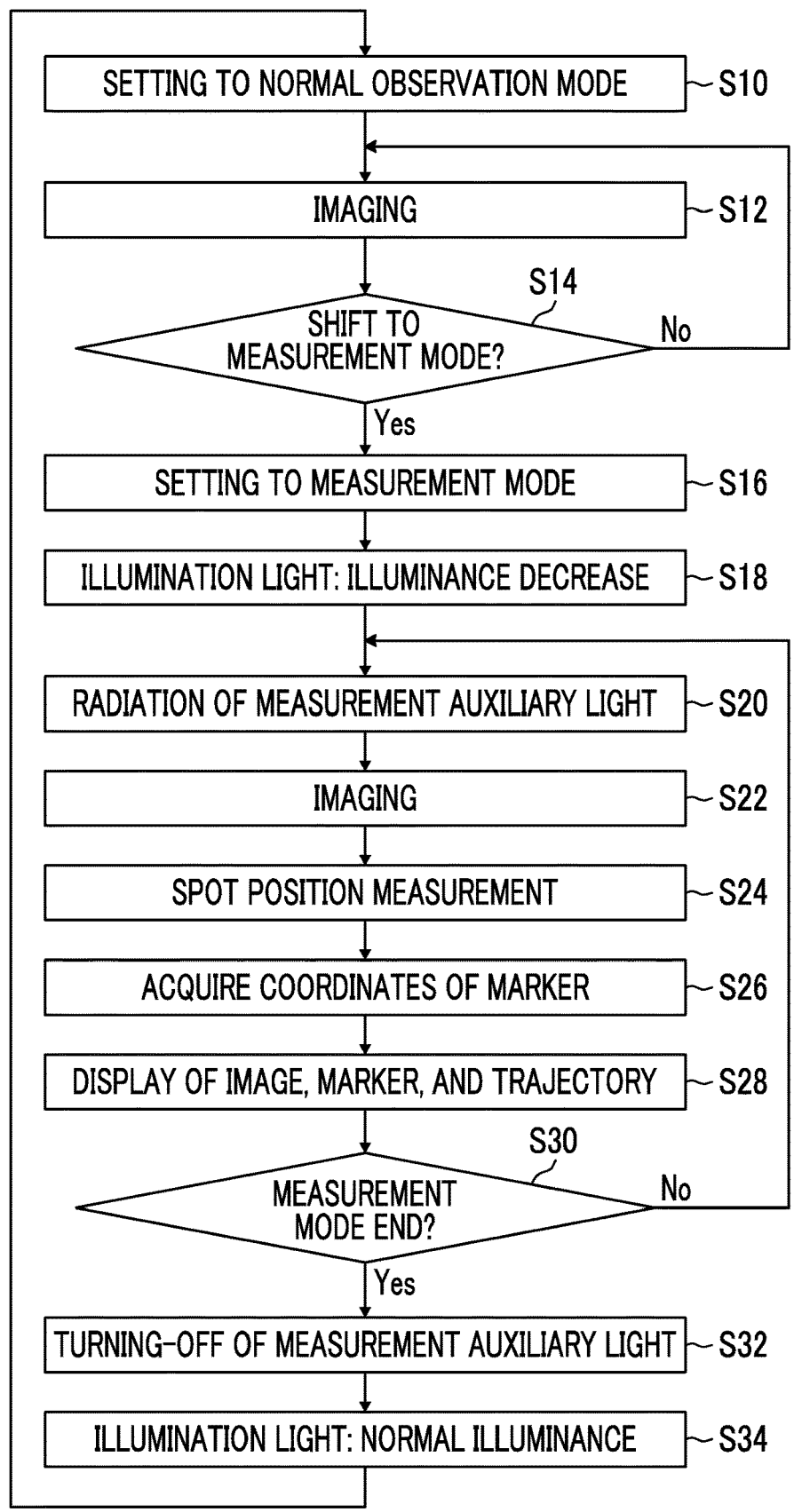
FIG. 8 is a flowchart illustrating processing of a measurement support method.

Next, the measurement support method for the subject using the endoscope system 10 will be described. FIG. 8 is a flowchart illustrating processing of the measurement support method.

First, the insertion part 104 of the endoscope body 100 is inserted into the subject, and the endoscope system 10 is set to a normal observation mode (Step S10). The normal observation mode is a mode in which the subject is irradiated with the illumination light radiated from the light source device 300 to acquire an image and the subject is observed. The setting to the normal observation mode may be automatically performed by the processor 200 at the time of the startup of the endoscope system 10 or may be performed in accordance with the operation of the operating part 208 by a user.

In a case where the endoscope system 10 is set to the normal observation mode, the illumination light is radiated to image the subject, and the obtained image is displayed on the monitor 400 (Step S12). As the image of the subject, a still image may be captured or a moving image may be captured. During the imaging, it is preferable to switch the type (the visible light or the infrared light) of the illumination light in accordance with the type of the subject, the purposes of observation, or the like. The user moves the insertion part 104 forward or backward and/or operates to bend the insertion part 104 to direct the distal end hard part 116 to an observation target while viewing an image displayed on the monitor 400 so that the subject to be measured is imaged.

Next, in Step S14, whether or not the normal observation mode shifts to a measurement mode is determined. This determination may be performed on the basis of the presence or absence of a user's operation via the operating part 208, or may be performed on the basis of the presence or absence of a switching command from the processor 200. Additionally, the processor 200 may alternately set the normal observation mode and the measurement mode at constant frame intervals (such as every one frame or every two frames). In a case where the determination of Step S14 is negative, the process returns to Step S12 and the imaging in the normal observation mode is continued, and in a case where the determination of Step S14 is positive, the process proceeds to Step S16 where switching to the measurement mode is performed.

The measurement mode is a mode in which the laser light (measurement auxiliary light) is radiated from the laser head 506 to form a spot on the subject, and a marker for measuring the size (length) of the subject on the basis of the image of the subject on which the spot is formed is generated and displayed. In the measurement mode, a circular marker (indicator figure) indicating the actual size of the measurement target is displayed. As described below in detail, the circular marker is displayed in different aspects between a case where the measurement is effective and a case where the measurement is not effective (refer to FIGS. 12A to 13C). In the measurement mode, information indicating a trajectory along which the spot moves on the image when the imaging distance is changed can be displayed depending on the setting of the display conditions described below (refer to FIGS. 13A to 13C, and 20). In the first embodiment, the red laser light is used as the measurement auxiliary light. However, since much of a digestive tract is reddish in an endoscope image, there is a case where the spot is not easily recognized depending on the measurement conditions. Thus, in the measurement mode, during the image acquisition and the position measurement of the spot, the illumination light is turned off or the illuminance is lowered to such a degree that the recognition of the spot is not affected (Step S18), and the measurement auxiliary light is radiated from the laser head 506 (Step S20). Such control can be performed by the processor 200 and the light source control unit 350.

In Step S22, an image of the subject on which the spot is formed with the measurement auxiliary light is captured. In a case where the observation distance is within a measurement range, the spot is formed within the imaging angle of view of the imaging optical system 130. As will be described below in detail, the positions of spots within an image (on the imaging element) are different in accordance with the observation distance, and the sizes (the numbers of pixels) of markers to be displayed are different in accordance with the positions of the spots.

<Change in Spot Positions According to Observation Distance>

Figure 9:
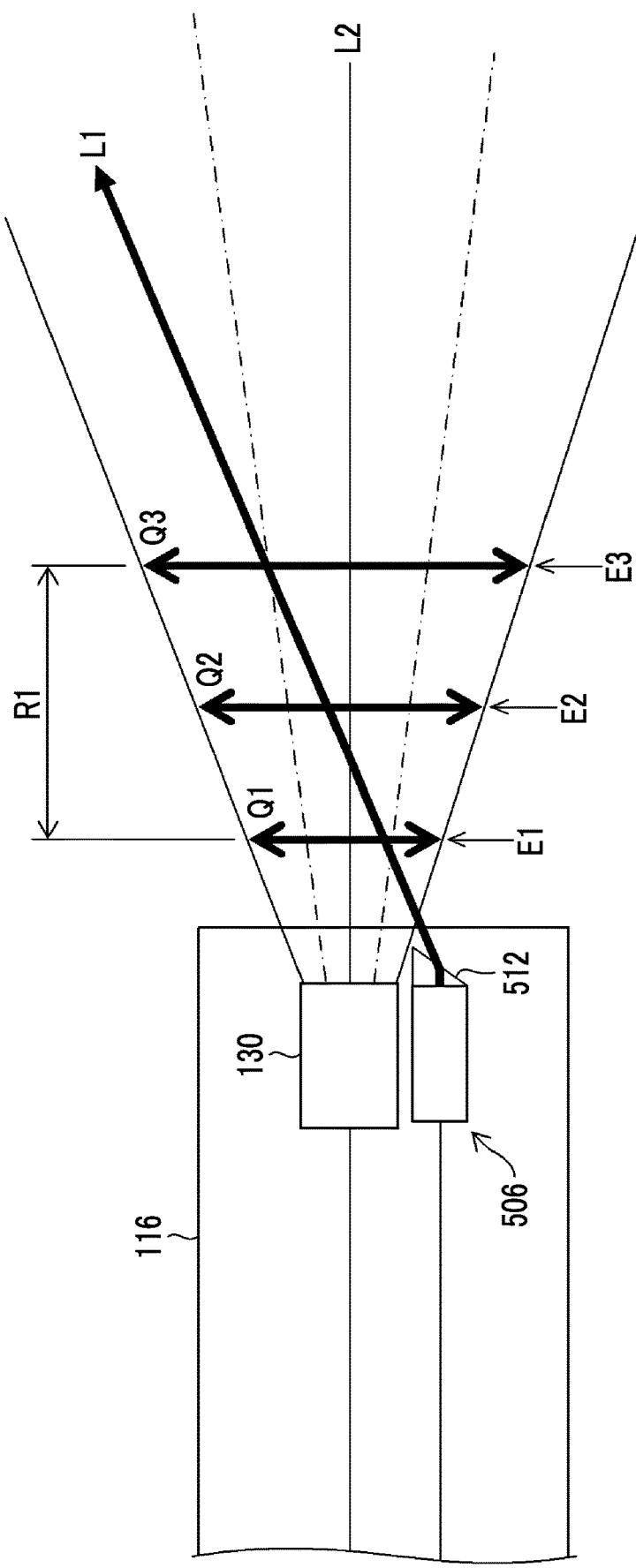
FIG. 9 is a view illustrating a state where the optical axis of the measurement auxiliary light crosses an imaging angle of view of the imaging optical system.

In the first embodiment, in a case where the optical axis L1 of the measurement auxiliary light is projected on the plane including the optical axis L2 of the imaging optical system, the optical axis L1 has the inclination angle, which is not 0 degrees with respect to the optical axis L2, and crosses the angle of view of the imaging optical system 130. Hence, the positions of spots in an image (imaging element) are different depending on the distance up to the subject. For example, as illustrated in FIG. 9 (a view illustrating a state where the distal end hard part 116 is seen from a lateral direction within the plane including the optical axis L1 and the optical axis L2), it is assumed that observation is possible in a range R1 of the observation distance. In this case, at a nearest end E1, a distance E2 in the vicinity of the center, and a farthest end E3 in the range R1, it can be understood that the positions of spots (points where the respective arrows and the optical axis L1 intersect each other) in imaging ranges (indicated by arrows Q1, Q2, and Q3) at the respective points are different from each other. In addition, in FIG. 9, the inside of solid lines is the imaging angle of view of the imaging optical system 130, and the inside of one-dot chain lines is a measurement angle of view. Measurement is performed at a central portion with a small aberration in the imaging angle of view of the imaging optical system 130. The range R1 and the measurement angle of view in FIG. 9 correspond to a "range where size measurement of a measurement target by a circular marker is effective in the captured image".

Figure 10:
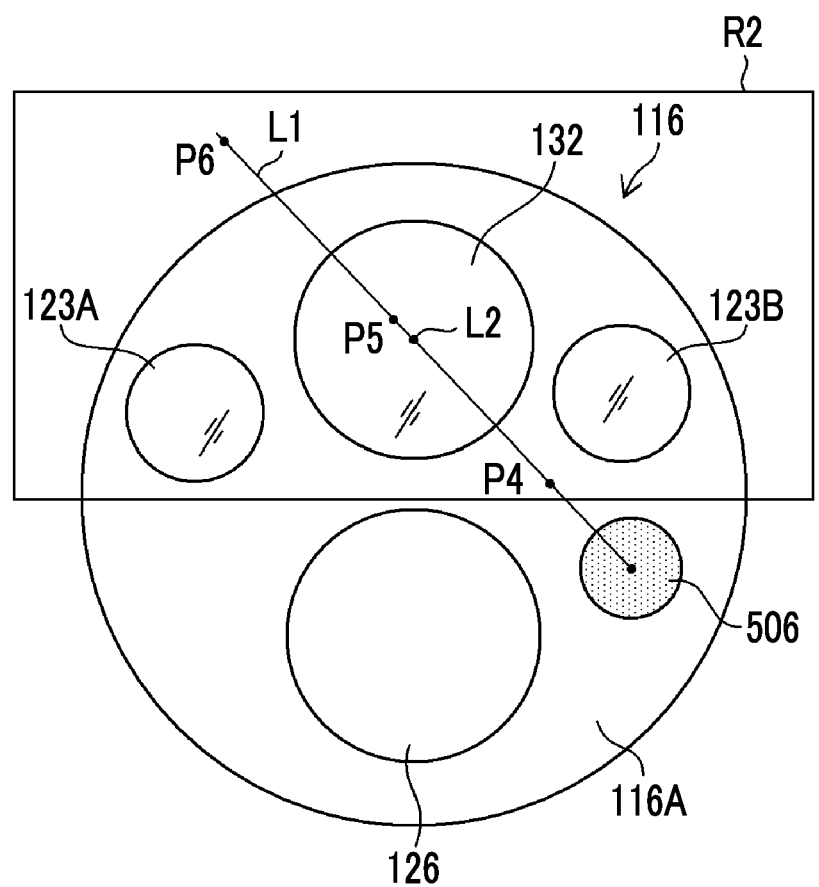
FIG. 10 is a view illustrating a state where a spot position is changed depending on a imaging distance.

FIG. 10 is a view illustrating a state where the distal end hard part 116 is seen from the front similarly to FIG. 6, and is a view virtually illustrating a relationship between the optical axis L2 of the imaging optical system 130, the optical axis L1 of the measurement auxiliary light, and an imaging range R2 of the imaging element 134. FIG. 10 illustrates a case where the optical axes L1 and L2 are present on the same plane and intersect each other on the plane. In an example of FIG. 10, spot positions P4, P5, and P6 (corresponding to cases where the observation distances are in the vicinity of the nearest end, in the vicinity of the center, and in the vicinity of the farthest end, respectively) according to the observation distance are illustrated.

As illustrated in FIG. 10, it can be understood that the spot position P4 in a case where the observation distance is in the vicinity of the nearest end and the spot position P6 in a case where the observation distance is in the vicinity of the farthest end are located opposite to each other with respect to the optical axis L2 of the imaging optical system 130. Hence, in the first embodiment, the sensitivity of the movement of the spot positions with respect to the change in the observation distance is high, and the size of subject can be measured with high accuracy.

In this way, although the spot positions within the captured image (on the imaging element 134) are different in accordance with the relationship between the optical axis L2 of the imaging optical system 130 and the optical axis L1 of the measurement auxiliary light, and the observation distance. However, the number of pixels indicating the same actual size (for example, diameter of 5 mm) increases in a case where the observation distance is near, and the number of pixels decreases in a case where the observation distance is far. Hence, as will be described below in detail, coordinates of points indicating a circular marker can be acquired by storing the position (coordinates) of a spot, and coordinates of points indicating a circular marker indicating an actual size of a measurement target (for example, a specific region such as a tumor and a lesion) in a subject in an association manner in the memory 139, and referring to information stored in accordance with the measured spot positions (coordinates). In the measurement processing, the information stored in the memory 139 may be expanded in the memory 212 and the information expanded in the memory 212 may be referred to. In the first embodiment, since it is not necessary to measure the observation distance itself in a case where the coordinates of the points indicating the circular marker are acquired, the configuration is simple, and the processing load is low.

Figure 11:
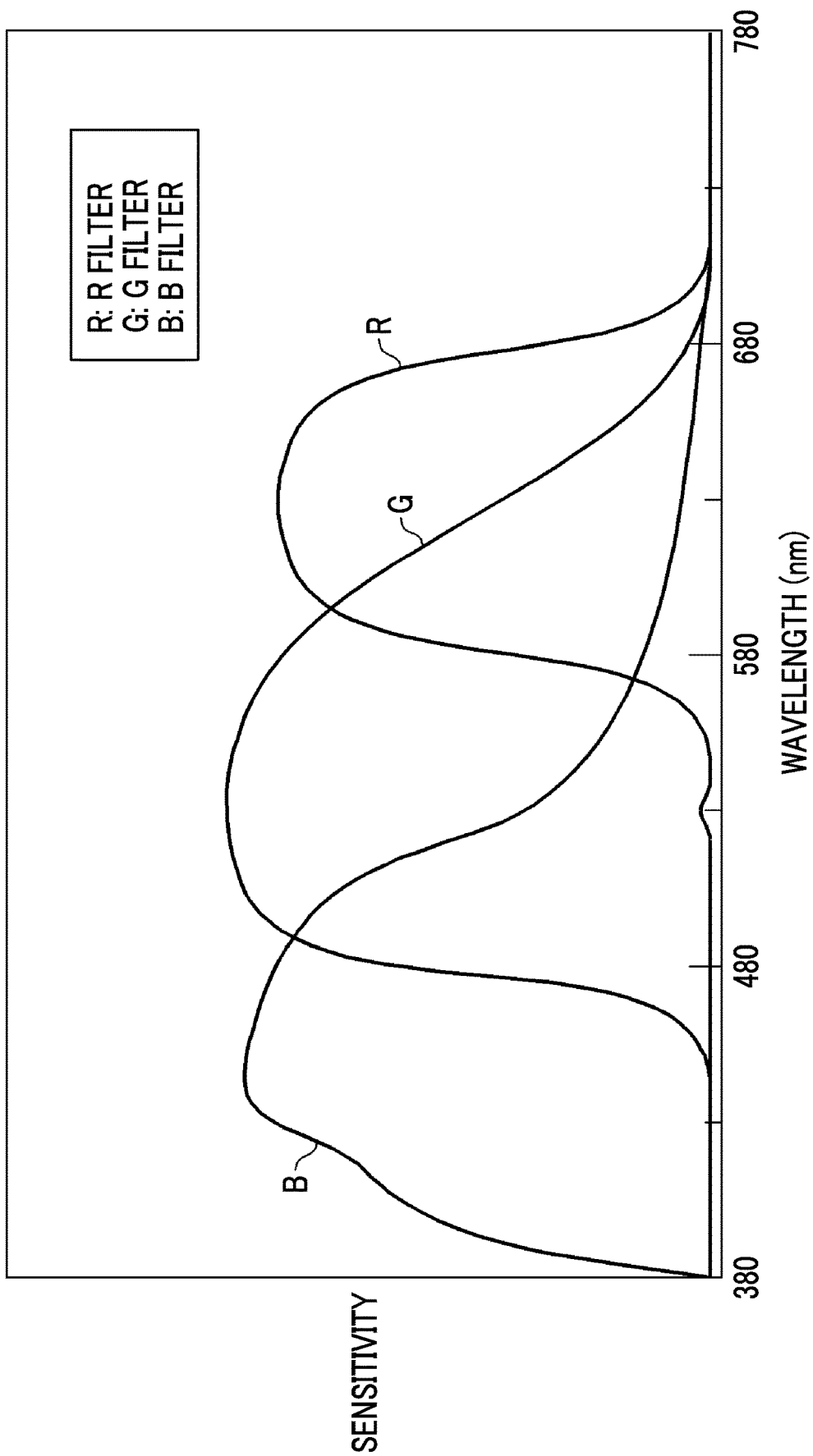
FIG. 11 is a view illustrating a relationship between a wavelength and a sensitivity of color filters.

Referring to the flowchart of FIG. 8, the position measurement of a spot (Step S24) on the imaging surface of the imaging element 134 will be described. The position measurement of the spot in Step S24 is performed by an image generated by pixel signals of pixels in which a color filter of red (R) color is disposed. Here, a relationship between the wavelength and sensitivity in color filters of respective colors (red, green, and blue) disposed in respective pixels of the imaging element 134 is as illustrated in FIG. 11. Additionally, the laser light emitted from the laser head 506 is red laser light with a wavelength of 650 nm. That is, the measurement of the spot positions is performed on the basis of the image generated by the image signals of the pixels (R pixels) in which a color filter of a red color with the highest sensitivity with respect to the wavelength of the laser light among red, green, and blue color filters is disposed. In this case, the position of the spot can be recognized at high speed by providing a threshold value to the signal intensity of the R pixels of bit map data or raw image format (RAW) data of the pixel signals to perform binarization and calculating the center of gravity of a white portion (a pixel having a higher signal intensity than the threshold value). In addition, in a case a spot is recognized by an actual image (an image generated by pixel signals of all colors), it is preferable that pixel signals of pixels (G pixels and B pixels) in which green and blue color filters are disposed are provided with threshold values, and only the pixels in which values of the pixel signals of the G pixels and the B pixels having the bit map data are equal to or smaller than the threshold values are extracted.

In addition, in the measurement mode, as described above, during the image acquisition (Step S22) and the position measurement (Step S24) of the spot, the illumination light is turned off or the illuminance is lowered to such a degree that the recognition of the spot is not affected (Step S18), and the measurement auxiliary light is radiated from the laser head 506 (Step S20). Accordingly, an image with a clear spot can be acquired, the position of the spot can be accurately measured, and a marker having a suitable size can be generated and displayed.

In Step S26, the processor 200 (the CPU 210 and the image processing unit 204) acquires coordinates of points indicating a circular marker. As described above, the sizes of markers on the monitor 400 are different in accordance with the positions of spots within an image (namely, on the imaging surface of the imaging element 134). Thus, coordinates of a spot, and coordinates of points indicating the circular marker indicating an actual size of the measurement target in the subject are stored in an association manner in the memory 139 (or the information of the memory 139 is acquired to be stored in the memory 212). The processor 200 refers to the memory 139 (or the memory 212) in accordance with the spot position measured in Step S24, and acquires the coordinates of the points indicating the circular marker. A procedure of obtaining a relationship between the spot positions and the coordinates of the points indicating the circular marker will be described below in detail. In addition, in a case where information indicating the movement trajectory of the spot is displayed, the processor 200 also acquires this information from the memory 139 (or the memory 212).

In Step S28, the observation image, the circular marker, and the like are displayed on the monitor 400 (display device) on the basis of the set display conditions (refer to an example of FIG. 20). As described below, the circular marker is displayed in different aspects between a measurement effective region and other regions.

<Display Aspect of Marker According to Effectiveness of Measurement>

Example 1

Figure 12A:
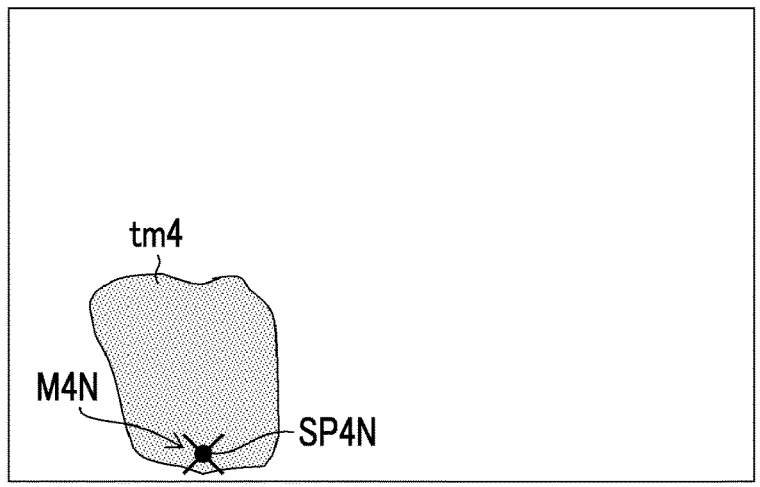
FIGS. 12A to 12C are views illustrating a state where a marker is displayed in different aspects between a case where measurement is effective and a case where measurement is not effective.
Figure 12B:
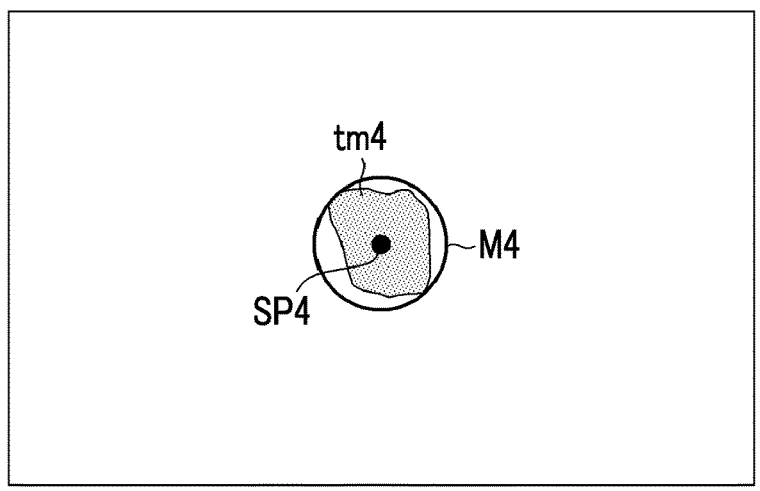
Figure 12C:
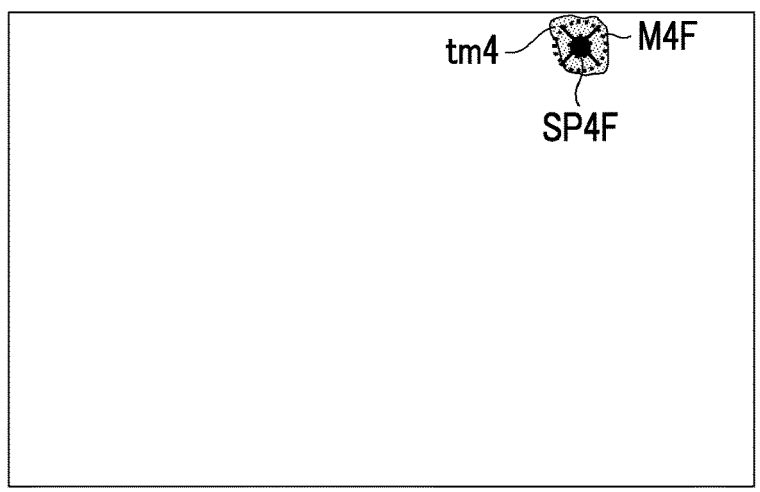

FIGS. 12A to 12C are views illustrating a state where the display aspects of the marker are changed between a region where measurement by the marker is effective and other regions. Specifically, in a case where a spot SP4N is present outside a range (on the nearest end side) of the measurement effective region as illustrated in FIG. 12A and in a case where a spot SP4F is present outside a range (on the farthest end side) of the measurement effective region as illustrated in FIG. 12C, since the measurement of a tumor tm4 by the marker is not effective, cross markers M4N and M4F are respectively displayed. Here, different kinds of a line may be used or different colors may be used for the markers on the nearest end side and the farthest end side. Meanwhile, in a case where a spot SP4 is present in a range where the measurement by a circular marker M4 (a marker having a shape different from the markers M4N and M4F) is effective as illustrated in FIG. 12B, the marker M4 is displayed using a solid line. The circular marker M4 and the markers M4N and M4F may be different in color.

Example 2

Figure 13A:
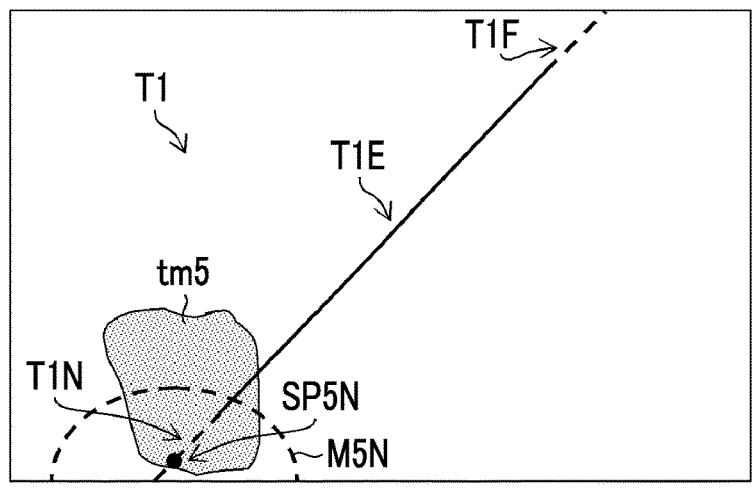
FIGS. 13A to 13C are other views illustrating a state where a marker is displayed in different aspects between a case where measurement is effective and a case where measurement is not effective.
Figure 13B:
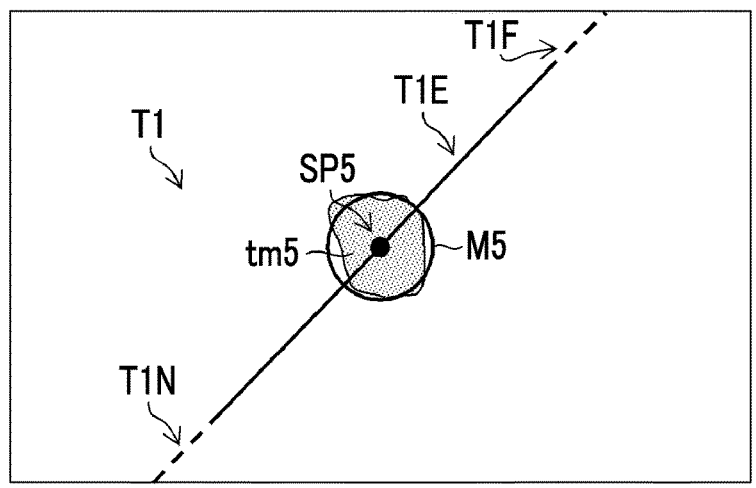
Figure 13C:
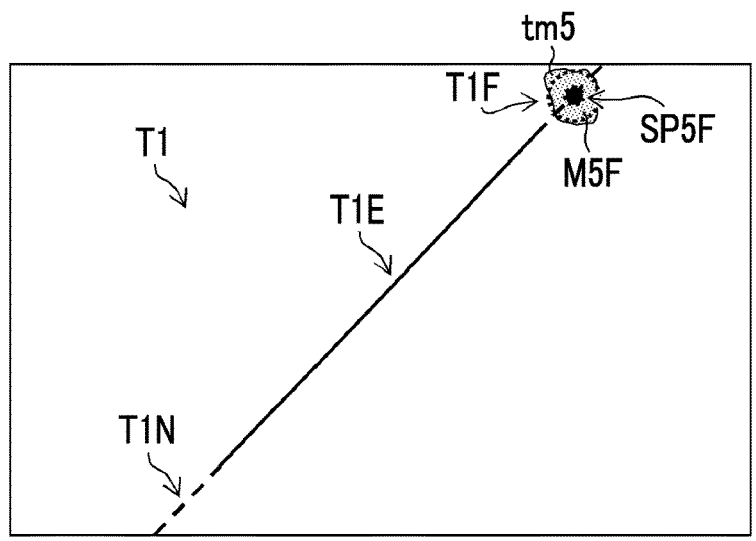

FIGS. 13A to 13C are other views illustrating a state where the display aspects of the marker are changed between a region where measurement by the marker is effective and other regions. In Example 1 of FIGS. 12A to 12C, the circular marker is displayed in the measurement effective region and the cross marker is displayed in other regions (the shape of the marker is changed). However, in the example of FIGS. 13A to 13C, a circular marker is displayed regardless of the region, and kinds of a line of the marker are changed between the measurement effective region and other regions. In addition, in Example 1, the movement trajectory of the spot is not displayed, but in Example 2, a case in which the movement trajectory is displayed is described. Specifically, in a case where a spot SP5N is present in a region T1N on the nearest end side of a movement trajectory T1 as illustrated in FIG. 13A and in a case where a spot SP5F is present in a region T1F on the farthest end side of the movement trajectory T1 as illustrated in FIG. 13C, since the measurement of a tumor tm5 by a circular marker M5N or M5F is not effective, the circular markers M5N and M5F are respectively displayed using dotted lines. In FIGS. 13A and 13C, the circular markers on the nearest end side and the farthest end side are displayed using dotted lines, but different kinds of a line (for example, dotted line and one-dot chain line) may be used or different colors (for example, red and black) may be used on the nearest end side and the farthest end side. Meanwhile, in a case where a spot SP5 is present in a range T1E where the measurement by a circular marker M5 is effective as illustrated in FIG. 13B, the circular marker M5 is displayed using a solid line (for example, white).

In the first embodiment, whether the measurement by the marker is effective or not can be easily determined by the display aspects of the marker as in Examples 1 and 2, and thus the measurement can be swiftly and easily performed.

In a case where a circular marker is displayed as in FIGS. 12A to 13C, the circular marker being displayed at a position away from the spot is inaccurate as an indicator, it is preferable that the circular marker is displayed in the vicinity of the spot (with the spot as a center) in the observation image. Circular markers having different actual sizes (for example, 3 mm, 5 mm, and the like) may be concentrically displayed, and other markers (for example, cross markers) may be displayed in addition to the circular markers. In addition, the circular marker is displayed by the processor 200 (the CPU 210 and the image processing unit 204) acquiring the information stored in the memory 139 (information storage unit). At the time of the display, the information stored in the memory 139 may be expanded in the memory 212, and the processor 200 may refer to the memory 212 (the same applies to the movement trajectory of the spot). As described above, the processor 200 acquires and displays the information stored in the endoscope body 100, and thus the processor 200 can cope with various endoscope bodies.

The display conditions (the type, number, actual size, and color of the marker, presence or absence of the display of the movement trajectory of the marker, and the like) can be set by the user's operation via the operating part 208 (display condition setting unit) and/or the monitor 400 which will be described below in detail (refer to FIGS. 17 to 20).

In a case where the image, the marker, and the like are displayed, the marker and the observation target (tumor and the like) are compared to measure the size of the observation target. As described above, since the circular marker is displayed in different aspects between the measurement effective region and other regions, the effectiveness of the measurement can be easily grasped using the display aspect of the circular marker, and thus effective measurement can be easily performed. At the time of the measurement, a release operation (an operation for instructing recording of an image) is performed on the proximal operating part 102 (or the operating part 208) as necessary, and the image on which a spot is formed is recorded in the image recording unit 207 (image recording unit). In a case where the image, the spot position, and the like are recorded in the image recording unit 207, as described below, processing such as displaying of a circular marker and the like can be performed offline (post-processing) (refer to FIGS. 22 to 25).

In a case where the measurement and recording of the image and the like are completed, in Step S30, whether the measurement mode is ended is determined. This determination may be performed on the basis of the user's operation via the operating part 208, or may be performed on the basis of the presence or absence of a switching command from the processor 200. Additionally, similarly to the case of shifting to the measurement mode, in a case where a certain number of frames have elapsed, the measurement mode may be automatically ended and may return to the normal observation mode. In a case where the determination of Step S30 is negative, the process return to Step S20 and the processing of Step S20 to Step S28 is repeated. In a case where the determination of Step S30 is positive, the process proceeds to Step S32 where the measurement auxiliary light is turned off, subsequently the illuminance of the illumination light is returned to normal illuminance in Step S34, and the mode returns to the normal observation mode (returning to Step S10). In addition, in a case where there is no hindrance in the observation in the normal observation mode, the measurement auxiliary light may not be turned off.

As described above, in the endoscope system 10 according to the first embodiment, since a circular marker having a size set according to the position of the spot in the image is displayed in the vicinity of the spot, and the circular marker is displayed in different aspects between a region where the measurement is effective and a region where the measurement is not effective, the effectiveness of the measurement can be easily grasped and the measurement can be swiftly and easily performed.

<Details of Processing of Measurement Support Method>

Hereinafter, processing of the measurement support method described above will be described in detail.

<Coordinates of Points Indicating Circular Marker>

In the first embodiment, a position of a spot, and coordinates of points indicating a circular marker in the imaging surface of the imaging element 134 are stored in an association manner in the memory 139 (information storage unit) or the memory 212 (information storage unit), and coordinates are acquired with reference to the memory 139 or the memory 212 in accordance with the measured spot position. Hereinafter, storage of the coordinates will be described.

<Storage of Coordinates of Marker>

In the first embodiment, coordinates of points indicating a circular marker are stored for a plurality of points in a trajectory along which the spot moves on the captured image when the observation distance (imaging distance) is changed. The movement trajectory of the spot in the captured image in a case where the imaging distance is changed is determined depending on the relationship between the optical axis L1 of the measurement auxiliary light and the optical axis L2 of the imaging optical system 130, and is a straight line in the case of the relationship illustrated in FIG. 10, but is distorted in accordance with distortion in a case where the distortion is present in the imaging optical system 130.

Figure 14:
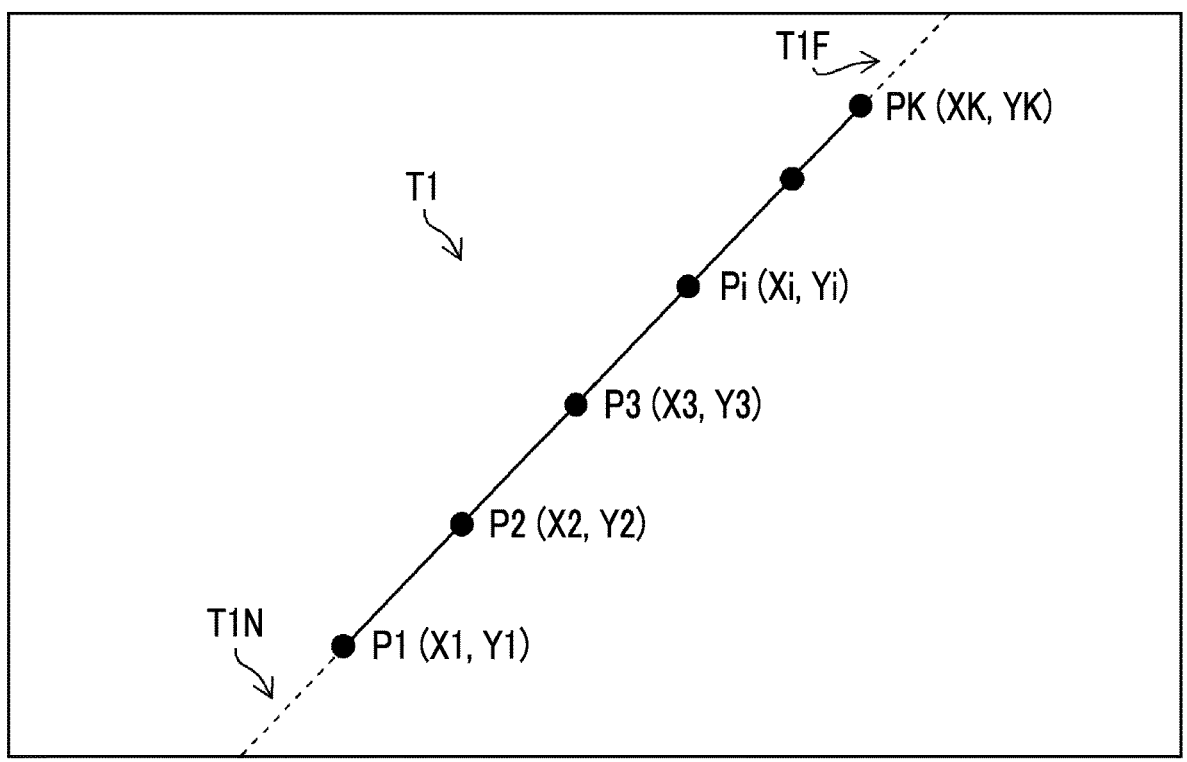
FIG. 14 is a view illustrating a state where coordinates of points indicating a circular marker are stored for a plurality of points in a movement trajectory of a spot.

FIG. 14 is a view illustrating an aspect of the coordinate storage, and illustrates a state where coordinates of points indicating a circular marker are stored for K points (points P1 to PK; K is an integer of 2 or more) in the movement trajectory T1 of a spot. The point P1 to the point PK are a range (a solid line portion of the movement trajectory T1; corresponding to the inside of the one-dot chain lines in FIG. 9) in which a size measurement by the circular marker is effective. The point P1 indicates a spot position in a case where the point P1 is the nearest end of the effective measurement range, and the point PK indicates a spot position in a case where the point PK is the farthest end. In addition, the movement trajectory T1 in FIG. 14 is virtually illustrated.

In a case where the spot is present in a dotted line portion of the movement trajectory T1 (the peripheral portion of the captured image), the distortion becomes large. In addition, there are problems in that a part of the circular marker is out of the image in a case where the spot is present on the nearest end side (a portion of a region T1N indicated by a dotted line) of the movement trajectory T1, or the marker becomes small in a case where the spot is present on the farthest end side (a portion of a region T1F indicated by a dotted line), and any of these cases is not suitable for measurement. Thus, in the first embodiment, coordinates are stored in correspondence with the range of the spot position (a portion of a region T1E indicated by a solid line) where the size measurement of the measurement target by the circular marker is effective.

Figure 15:
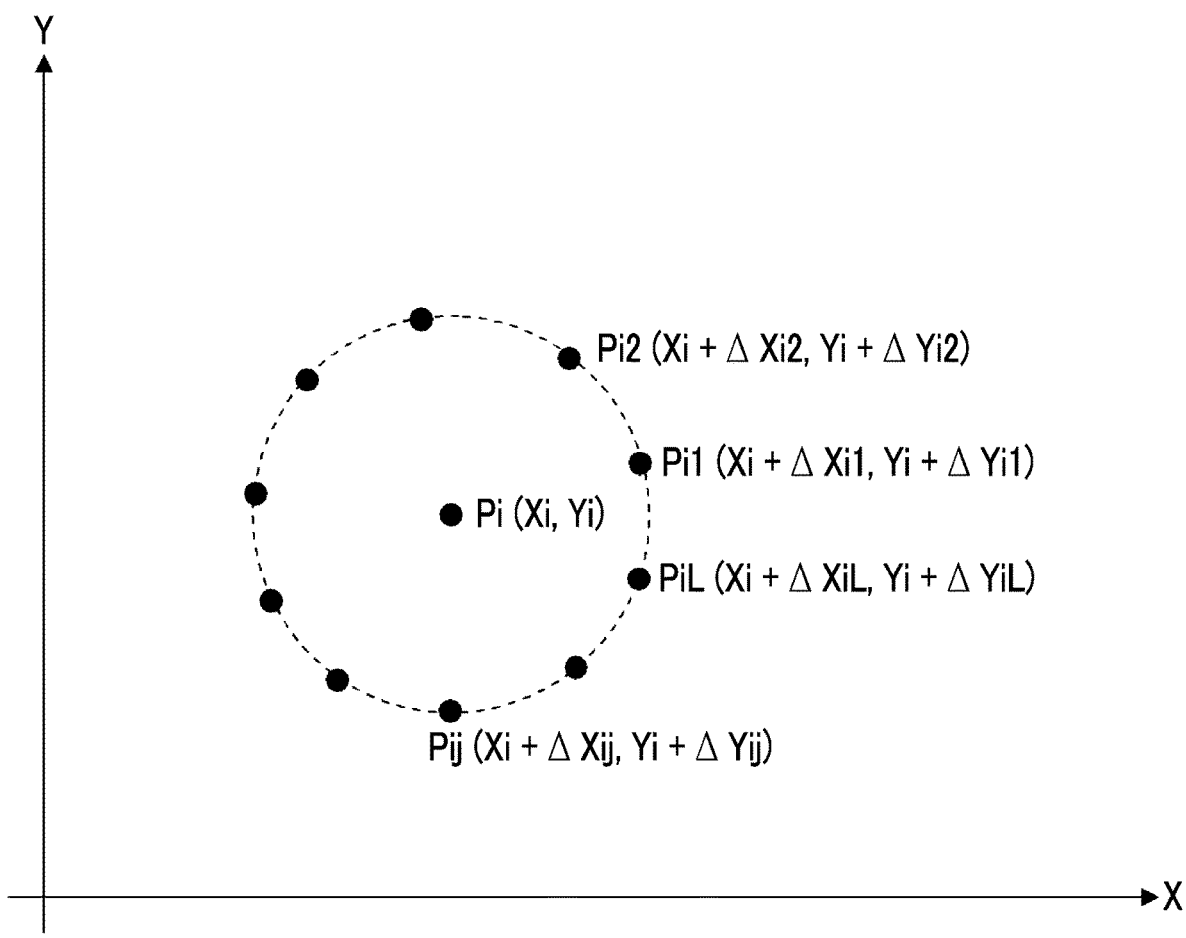
FIG. 15 is a view illustrating a relationship between a spot position and coordinates of points indicating a circular marker.

FIG. 15 is a view illustrating a relationship between a spot position and coordinates of points indicating a circular marker, and illustrates the circular marker with L points (points Pi1, Pi2, . . . , Pij, . . . , PiL; L is an integer) centered on a point Pi (the position of a spot). The value of L can be determined on the basis of the required shape accuracy of the marker, and an accurate marker can be displayed as the number of points increases. The L points may be connected to each other by a straight line or a curved line. Additionally, FIG. 16 is a view illustrating a state where the spot position and the coordinates of the points indicating the circular marker are stored in an association manner.

<Acquisition of Coordinates>

In a case where the circular marker is displayed, the processor 200 (the CPU 210 and the image processing unit 204) acquires coordinates of the points indicating the circular marker with reference to the memory 139 (information storage unit) or the memory 212 (information storage unit) on the basis of the measured coordinates of the spot. The "acquisition" herein includes using the stored coordinates and using the coordinates generated on the basis of the stored coordinates.

The coordinates of the L points indicating the circular marker as illustrated in FIG. 15 are stored for each of the K points (spot positions) which are the points P1 to PK illustrated in FIG. 14. For example, coordinates of the points Pi1 to PiL are stored for the point Pi on the movement trajectory T1. Specifically, as illustrated in FIG. 16, the spot positions and the coordinates of the points indicating the circular marker are stored in an association manner in the memory 139 (or the memory 212). In this case, the coordinates may be stored to correspond to each of the plurality of actual sizes (for example, 2 mm, 3 mm, 5 mm, 7 mm, and 10 mm), and the actual size of the displayed circular marker may be switched in accordance with the measurement purpose. As the number of spot positions (K in the examples of FIGS. 14 to 16) of which the coordinates are stored, and the number of points indicating the circular marker (L in the examples of FIGS. 14 to 16) increase, the circular marker can be more accurately displayed.

The coordinates of the points indicating the circular marker may be stored for some points (for example, K points of the points P1 to PK in the example of FIG. 14) on the movement trajectory T1. In this case, for the point (spot position) of which the coordinates are not stored, it is possible to acquire the coordinates of the marker by an aspect (first aspect) in which the coordinates stored for the points of which the distance from the measured spot position is within a threshold value are used. In addition, coordinates of the marker can be acquired by an aspect (second aspect) in which coordinates are acquired by interpolating the coordinates corresponding to two or more points that sandwich the measured spot, an aspect (third aspect) in which coordinates are acquired by extrapolating the coordinates corresponding to two or more points that do not sandwich the measured spot, and the like.

Meanwhile, coordinates may be stored for all points (pixels) on the movement trajectory T1, and the stored coordinates may be acquired as they are. In the case of using such aspects, distance calculation, interpolation calculation, and the like between the points can be omitted.

Meanwhile, coordinates may be stored for all points (pixels) on the movement trajectory T1, and the stored coordinates may be acquired as they are. In the case of using such aspects, distance calculation, interpolation calculation, and the like between the points can be omitted.

<Generation of Coordinates>

Coordinates of points (the points Pi1 to PiL in the example of FIG. 15) indicating the circular marker can be generated by the following method, for example. Specifically, a square grid chart is imaged while the imaging distance is changed. In this case, the proximal operating part is operated to position the spot at an intersection of the grid, and coordinates of four points on the top, bottom, right, and left side of the spot are measured. Coordinates of other points are generated by interpolating the measured coordinates of the point. In the chart to be imaged, it is preferable that the interval of the grid is equal to or smaller than the actual size, and the interval is as fine as possible. Additionally, in order to position the "four points on the top, bottom, right, and left side of the spot" described above at intersections of the grid, in the chart to be imaged, it is preferable that the interval of the grid is an interval (1/integer) of a desired actual size (in a case where the actual size of the circular marker has a diameter of 5 mm, the interval of the grid is 0.5 mm, 1 mm, 1.25 mm, 2.5 mm, or the like). In addition, coordinates of the points indicating a marker having another shape such as a cross may be generated on the basis of the measured spot position and the four points on the top, bottom, right, and left side of the spot.

<Setting of Screen Display Condition>

The display condition setting such as the captured image, the circular marker, the movement trajectory of the spot, and the like, and display aspects depending on the set conditions will be described. FIG. 17 is a view illustrating an example of an entire screen for setting screen display conditions. FIG. 17 illustrates condition names (regions C01 to C08), contents of the set condition (numerical value or the like; regions V01 to V08), and buttons A01 to A08 for the condition setting for items of the screen display conditions. The buttons B01, B02, and B03 provided in a lower portion of the screen are respectively for confirming the display condition, for canceling the condition change, and for clearing the condition change (returning to initial values). The screen of FIG. 17 is displayed on the monitor 400, and the display conditions can be set by the user's operation via a touch panel of the monitor 400 and/or a keyboard and a mouse (not illustrated) of the operating part 208. Such display condition setting may be performed at any time during the execution of the flowchart of FIG. 8. The layout and the display items of the display condition setting screen to be described below are examples of the display condition setting, and other aspects can be adopted as needed.

The regions C01 and V01 indicate whether a marker is displayed, and the display of the marker can be turned on or off by a selection operation via the button A01. The regions C02 and V02 indicate an actual size of a marker, and a size such as 3 mm or 5 mm can be selected by an operation via the button A02. The regions C03 and V03 indicate a display aspect of a marker in a measurement effective region, and the aspect such as a solid circle or a solid concentric circle can be selected by an operation via the button A03 (refer to FIG. 18). The regions C04 and V04 indicate a color of a marker in a measurement effective region, and a color such as white or blue can be selected by an operation via the button A04. The regions C05 and V05 indicate a display aspect of a marker in a measurement non-effective region, and an aspect such as a dotted circle, a solid cross, or a dotted cross can be selected by a selection operation via the button A05 (refer to FIG. 19). The regions C06 and V06 indicate a color of a marker in a measurement non-effective region, and a color such as red or black can be selected by an operation via the button A06. The regions C07 and V07 indicate whether a movement trajectory of a spot is displayed, and ON or OFF (displayed or not displayed) can be selected by an operation via the button A07. The regions C08 and V08 indicate whether a measurement effective region is displayed to be identified (for example, as illustrated in FIGS. 13A to 13C, the measurement effective region is displayed using a solid line and other regions are displayed using dotted lines), and ON or OFF (displayed to be identified or not displayed to be identified) can be selected by an operation via the button A08.

<Specific Example of Display Condition Setting>

Figure 18:
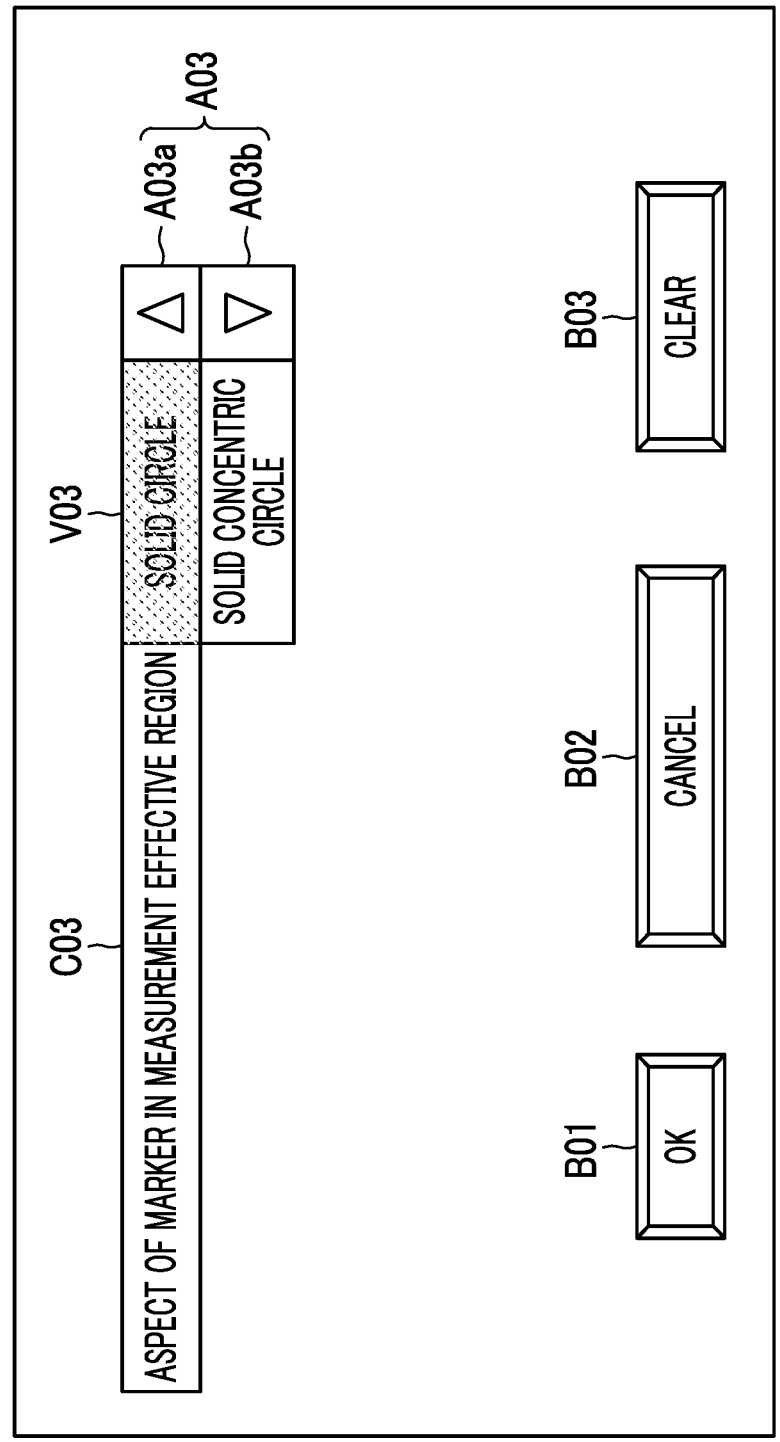
FIG. 18 is another view illustrating an example of the display condition setting screen.

The specific example of the display condition setting operation will be described. FIG. 18 is a view illustrating an example of a screen for setting the display aspect of the marker in the measurement effective region. In the screen of FIG. 17, in a case where the button A03 is designated by an operation on the touch panel of the monitor 400 or an operation via the operating part 208 (the same applies to other items), the region V03 is displayed in a pull-down manner and transitions to a state of FIG. 18. The illustration for items other than the display aspect of the marker in the measurement effective region in FIG. 18 is omitted. In FIG. 18, conditions (in this case, solid circle and solid concentric circle) that can be set as display aspects in the measurement effective region are displayed in the region V03, and the user moves a selection range up and down with buttons A03a and A03b to select the aspect (for example, solid circle) and determines the display aspect by designating the button B01 (OK button).

Figure 19:
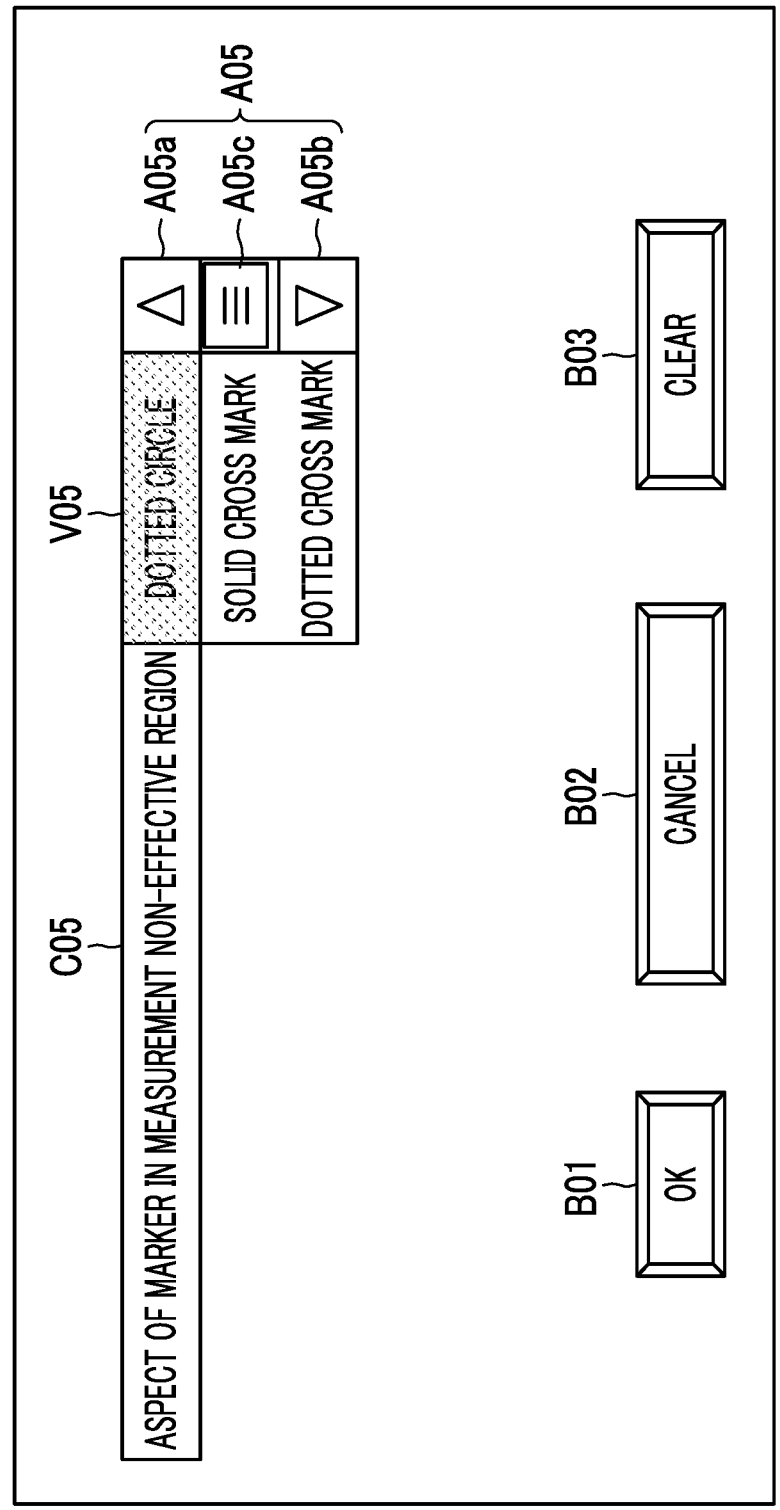
FIG. 19 is still another view illustrating an example of the display condition setting screen.

FIG. 19 is a view illustrating an example of a screen for setting the display aspect of the marker in the measurement non-effective region (region in which measurement by a marker is not effective). In the screen of FIG. 17, in a case where the button A05 is designated, the region V05 is displayed in a pull-down manner and transitions to a state of FIG. 19 (the illustration for items other than the display aspect of the marker in the measurement non-effective region is omitted). In the example of FIG. 19, the display aspect can be selected from "a dotted circle, a solid cross, and a dotted cross", and the user moves a selection range up and down with buttons A05a and A05b and a slide bar A05c to select the display aspect (a dotted circle in FIG. 19; refer to FIGS. 13A and 13C), and designates the button B01.

In the setting of the display condition described above, in a case where the conditions respectively set for the items do not match, a warning message may be output via the monitor 400 and/or the speaker 209A.

<Setting of Display Condition by Other Operation Means>

In the above-described example, the case in which the display conditions of the marker are set by the touch panel of the monitor 400 and/or a keyboard and a mouse (not illustrated) of the operating part 208 has been described. However, the display conditions may be set by other operation means. For example, the display condition may be set by assigning a function to the function button BT3 of the proximal operating part 102. In addition, the display condition may be set by a foot pedal, a voice input, a gaze input, a gesture input, and the like. The user may not be able to freely move both hands during the operation of the endoscope body 100, and in such a case, the operation means is effective.

<Specific Example of Screen Display>

An example of the screen display with the conditions illustrated in FIG. 17 is illustrated in FIG. 20. As illustrated in FIG. 20, the screen displayed on the monitor 400 is constituted of an image display region D01 and an information display region D02. In the image display region D01, a spot SP1 is formed on a tumor tm1, and a circular marker M1 (actual size with a diameter of 5 mm) centered on the spot SP1 is displayed in white. In addition, the movement trajectory T1 of the spot is displayed, and is displayed in different aspects between a region T1E where measurement by the circular marker M1 is effective and other regions (a region T1N on the nearest end side and a region T1F on the farthest end side). Markers M1N and M1F are displayed at end points of the region T1E. The "region where measurement is effective" in the identification display is a region (corresponding to the range R1 of FIG. 9) which is in the vicinity of the center of the captured image and in which the influence of the distortion of the imaging optical system 130 is small and the marker does not extend beyond the image or become too small. In such a region, it is possible to perform accurate measurement. In the identification display of the movement trajectory, without being limited to the aspect of using the solid line and the dotted line as in FIG. 20, other kinds of a line may be used, and the thickness of the line, color, a figure and/or a symbol to be used, and the like may be changed.

Figure 21A:
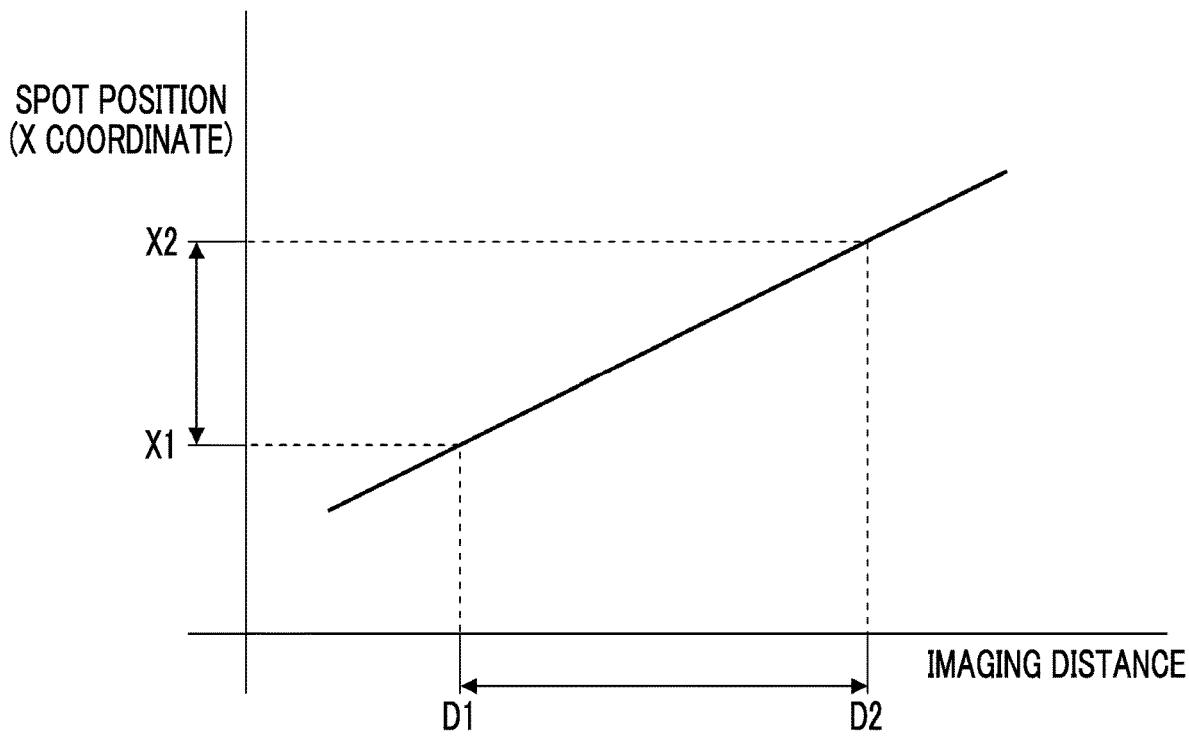
FIGS. 21A and 21B are views for describing a measurement effective region.
Figure 21B:
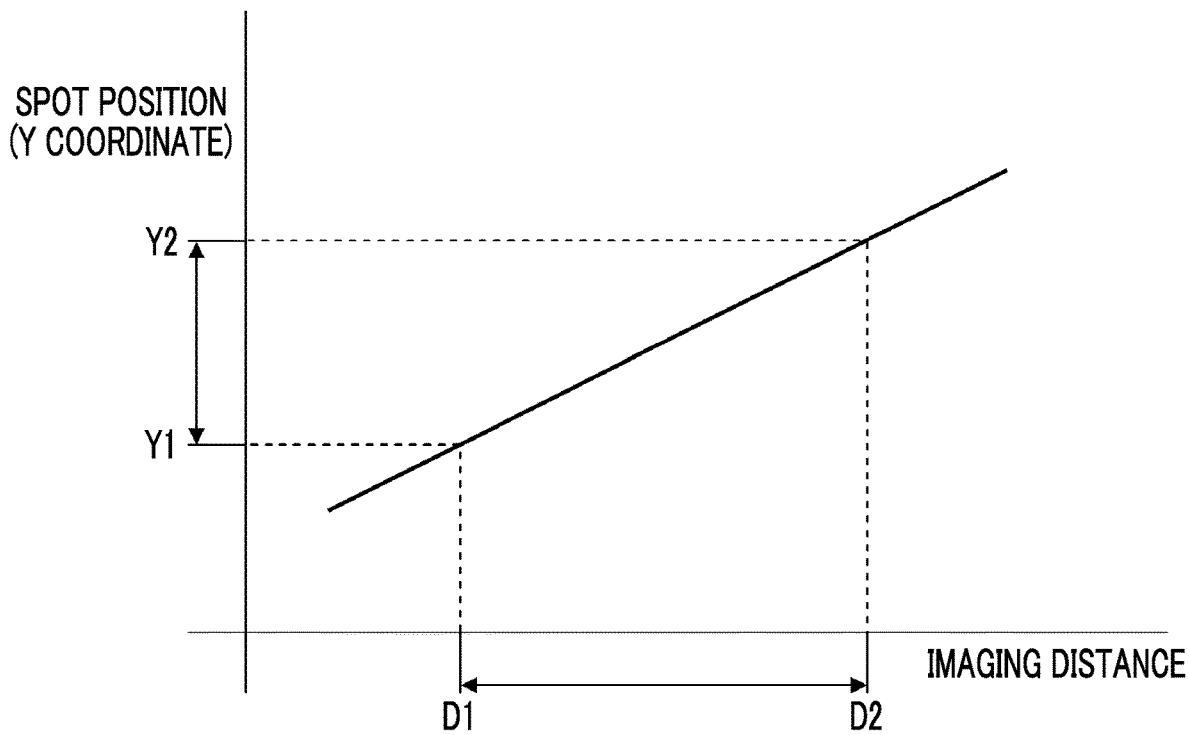

The above-described "region where measurement by a marker is effective" (measurement effective region) may be set to a part of the image or may be set for a range of the imaging distance. For example, a grid chart on which a spot is formed is imaged while the imaging distance is changed, the size of the grid, the distortion degree of the grid, and the like are measured at each distance, and the measurement effective region can be set on the basis of the measurement result. FIG. 21A conceptually illustrates a measurable range (D1 to D2) set for the imaging distance in the above-described procedure, and spot positions (X coordinate is from X1 to X2) corresponding to the measurable range. Further, FIG. 21B conceptually illustrates the measurable range (D1 to D2) set for the imaging distance, and spot positions (Y coordinate is from Y1 to Y2) corresponding to the measurable range. In the example of FIGS. 21A and 21B, in a case where the X coordinate of the spot positions is from X1 to X2 and the Y coordinate thereof is from Y1 to Y2 (an inside of the measurable region) and in a case where the imaging distance is within the measurable range (imaging distance is from D1 to D2), it is determined that "measurement by the marker is effective". Such information of the measurement effective region is stored in the memory 139 (information storage unit), and the processor 200 (the CPU 210 and the image processing unit 204) can acquire such information to determine "whether measurement by the marker is effective". By determining the effectiveness of the measurement on the basis of the information of the endoscope body 100 connected to the processor 200 in this manner, the processor 200 can cope with various endoscopes.

Referring back to FIG. 20, in the information display region D02, the fact that the endoscope system 10 is the "measurement mode" is displayed in a region D02A and current display conditions are displayed in a region D02B. In a case where the button B04 is designated, the mode is changed to the normal observation mode, and in a case where the button B05 is designated, the display condition setting screen as in FIG. 17 is displayed.

In the endoscope system 10 according to the first embodiment, the display conditions can be easily checked and changed by the above-described information display region D02, and thus the measurement can be swiftly and easily performed. The information display region D02 may be a separate screen, and the image display region D01 may be widened by hiding or reducing the information display region D02 during the observation mode.

<Offline Processing by Recording Image>

Figures 22, 23:
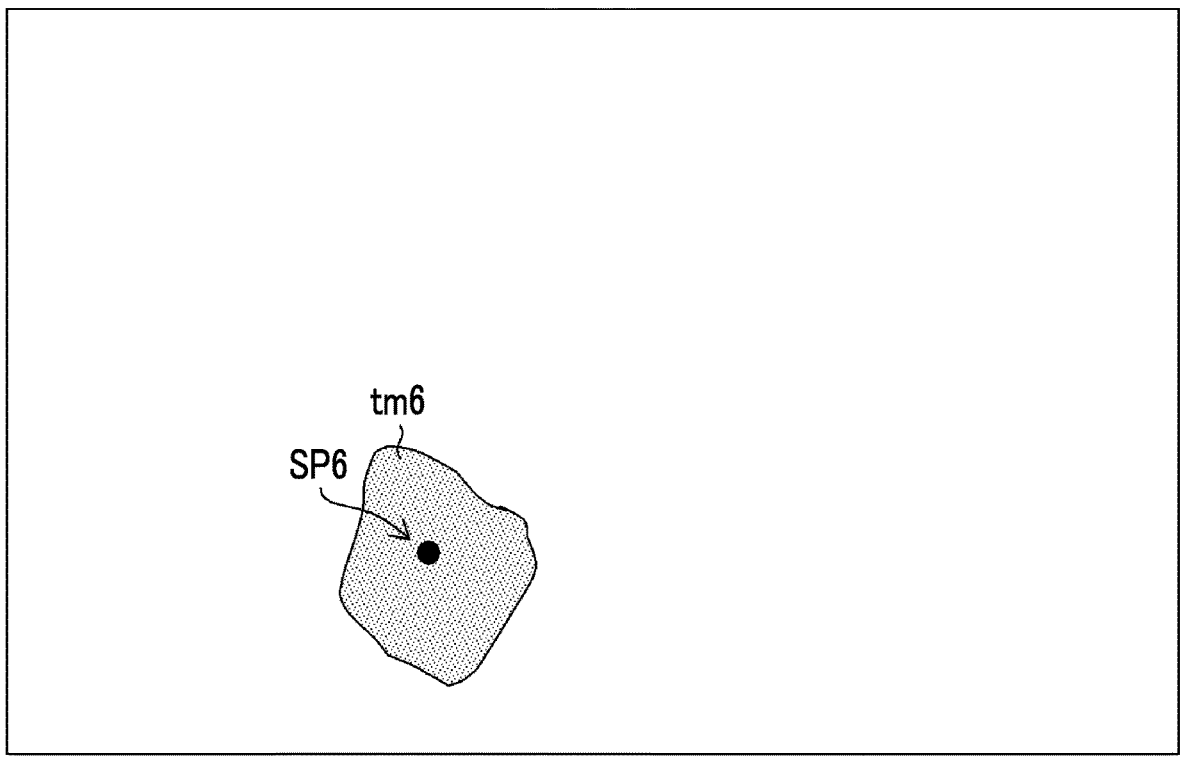
FIG. 22 is a view illustrating an image on which a spot is formed.
FIG. 23 is a view illustrating a state where an image on which a spot is formed is stored.
Figures 24, 25:
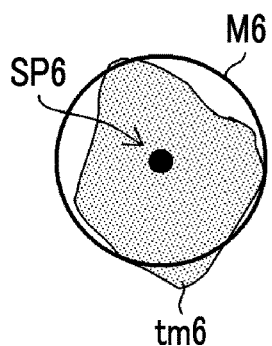
FIG. 24 is a view illustrating a state where a marker read from an image recording unit is displayed to be superimposed on an image of a subject.
FIG. 25 is a view illustrating a state where an image of a subject and coordinates of points indicating a marker are stored in an association manner.

In the endoscope system 10 according to the first embodiment, processing such as the marker display or the like and the measurement based on the processing may be performed in real time (display of a marker or a trajectory for each time an image on which a spot is formed is acquired or for every plural frames), or offline processing (post-processing) may be performed as described below. In order to perform the offline processing, an image on which a spot SP6 is formed on a tumor tm6 as in FIG. 22 is stored in the image recording unit 207. In this case, as illustrated in FIG. 23, the image (image file) and the spot position (coordinates) are recorded in an association manner. As described above, the spot positions and the coordinates of the points indicating the circular marker are stored in an association manner in the memory 139 (or the memory 212) (refer to FIG. 16). Accordingly, the coordinates of the points indicating the circular marker can be acquired by referring to the memory 139 (or the memory 212) on the basis of the spot positions recorded in association with the image, and thus the circular marker can be displayed to be superimposed on the image read from the image recording unit 207. FIG. 24 is an example of display by the offline processing, and the circular marker M6 centered on the spot SP6 is displayed to be superimposed on an image of the tumor tm6.

In addition to the above-described aspects, the image and the circular marker may be recorded in an association manner. For example, as illustrated in FIG. 25, an image (image file), a spot position (coordinates), and coordinates of points indicating a circular marker (which can be acquired by referring to the memory 139 or the memory 212) are recorded in an association manner in the image recording unit 207. Accordingly, the recorded image and the recorded coordinates of the points indicating the circular marker can be read and the circular marker can be displayed to be superimposed on the image (refer to FIG. 24).

As described above, by recording the captured image, the spot position, the coordinates of the points indicating the circular marker, and the like in an association manner, the post-processing such as the display of the circular marker or the like and the measurement can be performed, and thus it is possible to shorten the time during which the endoscope is inserted into the subject and thus to reduce the burden on the subject. As the image or the like used for the measurement, not only the images recorded in the image recording unit 207 may be used, but also images acquired from a non-temporary recording medium such as a compact disk (CD) or a digital versatile disc (DVD) via the image input interface 205 (refer to FIG. 2) may be used.

<Operation Using Movement Trajectory of Spot>

Figure 26A:
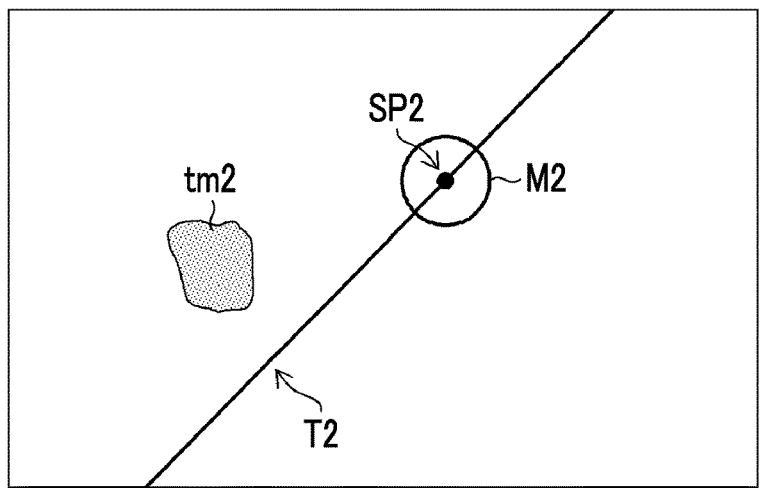
FIGS. 26A to 26C are views illustrating procedures of an operation using a movement trajectory of a spot.
Figure 26B:
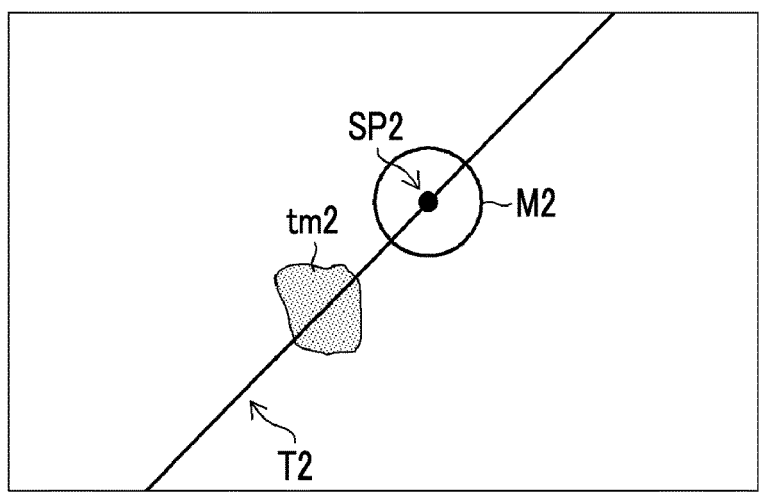
Figure 26C:
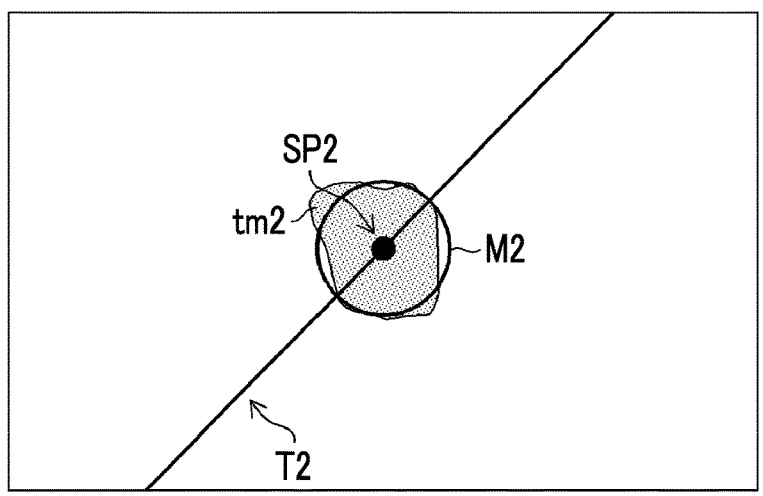

An operation using a movement trajectory displayed when the movement trajectory of the spot is displayed on the screen will be described. First, the operator operates the proximal operating part 102 to change the orientation of the distal end hard part 116 vertically and horizontally, and finds a lesion by screening (circular observation: Procedure 1). The state of Procedure 1 is illustrated in FIG. 26A. In the state of Procedure 1, a spot SP2 and a circular marker M2 (centered on the spot SP2) are present at a position separated from a tumor tm2, and the circular marker M2 is not effective as a measurement indicator. Then, the operator operates the proximal operating part 102 to change the orientation of the distal end hard part 116 vertically and horizontally, and causes the tumor tm2 to be placed on a movement trajectory T2 of the spot as in FIG. 26B (Procedure 2). Since the movement trajectory T2 indicates a movement trajectory of a spot in a case where the imaging distance is changed, the spot SP2 can be placed on the tumor tm2 by pushing and pulling the insertion part 104 from the state of Procedure 2. In the first embodiment, since the lower left in FIGS. 26A to 26C is the nearest end side of the imaging distance and the upper right in FIGS. 26A to 26C is the farthest end side, the spot SP2 is moved to the nearest end side on the movement trajectory T2 by pulling the insertion part 104 toward the proximal side from the state in FIG. 26B, and the spot SP2 can be placed on the tumor tm2 as in FIG. 26C (Procedure 3). Since the circular marker M2 is superimposed on the tumor tm2 by Procedure 3, the operator compares the actual size (for example, 5 mm) of the circular marker M2 with the tumor tm2 to measure the size of the tumor tm2 (Procedure 4). Further, a release operation (an operation for instructing recording of an image) is performed on the proximal operating part 102 (or the operating part 208) as necessary, and the image on which the spot Sp2 is formed is recorded in the image recording unit 207 (image recording unit) (Procedure 5). As described below in detail, in a case where an image, a spot position, and the like are recorded in the image recording unit 207, processing such as display of a circular marker and the like can be performed offline (post-processing) (refer to FIGS. 22 to 25).

In this manner, by displaying the circular marker and the movement trajectory of the spot in the vicinity of the spot, the operator can easily grasp how the spot and the circular marker move by the operation of the endoscope, and can swiftly and easily perform measurement.

<Others>

The measurement support device, the endoscope system, and the processor for an endoscope system according to the embodiments of the invention can also be applied to cases where subjects, which are not living bodies, such as a pipe, are measured in addition to measuring the subject that is a living body. Additionally, the measurement support device according to the embodiments of the invention can be applied not only to the endoscope but also to the cases of measuring the dimensions and shapes of an industrial part or the like.

Although the embodiments of the invention have been described above, it is obvious that the invention is not limited to the above-described aspects, and various modifications can be made without departing from the spirit of the invention.

EXPLANATION OF REFERENCES

10: endoscope system
100: endoscope body
102: proximal operating part
104: insertion part
106: universal cable
108: light guide connector
109: electrical connector
112: flexible part
114: bending part
116: distal end hard part
116A: distal-end-side end surface
123: illumination unit
123A: illumination lens
123B: illumination lens
126: forceps port
130: imaging optical system
132: imaging lens
134: imaging element
136: driving circuit
138: AFE
139: memory
170: light guide
200: processor
202: image input controller
204: image processing unit
205: image input interface
206: video output unit
207: image recording unit
208: operating part
209: sound processing unit
209A: speaker
210: CPU
212: memory
300: light source device 310: light source
310A: visible light source
310B: infrared light source
330: stop
340: condensing lens
350: light source control unit
400: monitor
500: laser module
501: fiber covering
502: laser light source module
503: condensing lens
504: optical fiber
506: laser head
507: reinforcing member
508: ferrule
509: housing
510: GRIN lens
512: prism
A01: button
A02: button
A03: button
A03a: button
A03b: button
A04: button
A05: button
A05a: button
A05c: slide bar
A06: button
A07: button
A08: button
AL1: apex angle
B01: button
B02: button
B03: button
B04: button
B05: button
BT1: air-supply and water-supply button
BT2: suction button
BT3: function button
C01: region
C02: region
C03: region
C04: region
C05: region
C06: region
C07: region
C08: region
D01: image display region
D02: information display region
D02A: region
D02B: region
E1: nearest end
E2: distance
E3: farthest end
IA: imaging range
L1: optical axis
L2: optical axis
M1: circular marker
M1N: marker
M2: circular marker
M4: circular marker
M4N: marker
M5: circular marker
M5N: circular marker
M6: circular marker
P4: spot position
P5: spot position
P6: spot position
Q1: arrow
Q2: arrow
Q3: arrow
R1: range
R2: imaging range
S10 to S34: respective steps of measurement support method
SP0: spot
SP1: spot
SP2: spot
SP4: spot
SP4F: spot
SP4N: spot
SP5: spot
SP5F: spot
SP5N: spot
SP6: spot
T1: movement trajectory
T1E: region
T1F: region
T1N: region
T2: movement trajectory
V01: region
V02: region
V03: region
V04: region
V05: region
V06: region
V07: region
V08: region
tm: tumor
tm1: tumor
tm2: tumor
tm4: tumor
tm5: tumor
tm6: tumor

What is claimed is:

1. An endoscope system comprising:
a measurement support device comprising:
a head configured to emit measurement auxiliary light;
an imaging unit configured to capture an image of a subject on which a spot is formed by the measurement auxiliary light via an imaging optical system and an imaging element; and
a processor configured to measure a position of the spot in the image,
wherein the processor is configured to display an indicator figure, which indicates an actual size of a specific region in the subject and has a size set according to the position of the spot in the image, in the vicinity of the position of the spot in the image of the subject; and
an endoscope including
a memory configured to store information indicating the indicator figure;
an insertion part which is to be inserted into the subject, and has a distal end hard part, a bending part connected to a proximal end side of the distal end hard part, and a flexible part connected to a proximal end side of the bending part, and
an operating part connected to a proximal end side of the insertion part, wherein the head and an imaging lens that forms an optical image of the spot on the imaging element are provided in the distal end hard part, wherein, in a case where an optical axis of the measurement auxiliary light is projected on a plane including an optical axis of the imaging optical system, the head emits the measurement auxiliary light that has an inclination angle, which is not 0 degrees with respect to the optical axis of the imaging optical system, and crosses an angle of view of the imaging optical system, and in a case where the indicator figure is displayed in the vicinity of the measured position of the spot, the processor displays the indicator figure in different aspects between a case where measurement of the specific region by the displayed indicator figure is effective and a case where measurement of the specific region by the displayed indicator figure is not effective.

2. The endoscope system according to claim 1,
wherein, in a case where the position of the spot is within a measurable region set for the image, the processor determines that measurement of the specific region by the indicator figure is effective.

3. The endoscope system according to claim 1,
wherein, in a case where an imaging distance of the image calculated on the basis of the position of the spot is within a measurable range, the processor determines that measurement of the specific region by the indicator figure is effective.

4. The endoscope system according to claim 1,
wherein the processor displays the indicator figure by changing at least one of a color or a shape of the indicator figure between a case where measurement of the specific region by the indicator figure is effective and a case where measurement of the specific region by the indicator figure is not effective.

5. The endoscope system according to claim 1,
wherein the processor is configured to record the image of the subject on which the spot is formed,
wherein the processor reads the image of the subject recorded in the processor, and displays the indicator figure to be superimposed on the read image of the subject.

6. The endoscope system according to claim 5,
wherein the processor records the image of the subject and the indicator figure in an association manner, and
the processor reads the indicator figure and the image of the subject which are recorded in the processor, and displays the read indicator figure to be superimposed on the read image of the subject.

7. The endoscope system according to claim 1,
wherein the processor displays, as the indicator figure, a circle indicating the actual size, which is centered on the spot, to be superimposed on the image.

8. The endoscope system according to claim 1,
wherein the processor displays information indicating a trajectory along which the spot moves on the image when an imaging distance of the image is changed, to be superimposed on the image.

9. The endoscope system according to claim 1,
wherein the processor is configured to set a display condition of the indicator figure.

10. The endoscope system according to claim 1,
wherein the processor is configured to acquire information of the endoscope,
wherein the processor determines whether measurement of the specific region by the displayed indicator figure is effective on the basis of the acquired information.

\* \* \* \* \*